(12) United States Patent
Le Hir de Fallois et al.

(10) Patent No.: US 8,314,146 B2
(45) Date of Patent: Nov. 20, 2012

(54) THIOAMIDE COMPOUNDS, METHOD OF MAKING AND METHOD OF USING THEREOF

(75) Inventors: Loic Patrick Le Hir de Fallois, Chapel Hill, NC (US); Hyoung Ik Lee, Cary, NC (US); Philip Reid Timmons, Durham, NC (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 13/086,161

(22) Filed: Apr. 13, 2011

(65) Prior Publication Data

US 2011/0190231 A1   Aug. 4, 2011

Related U.S. Application Data

(62) Division of application No. 12/582,486, filed on Oct. 20, 2009, now Pat. No. 7,964,621.

(60) Provisional application No. 61/107,114, filed on Oct. 21, 2008.

(51) Int. Cl.
*A61K 31/277* (2006.01)
*C07C 255/50* (2006.01)

(52) U.S. Cl. ........................................ 514/522; 558/415

(58) Field of Classification Search .................. None
See application file for complete search history.

(56) References Cited

U.S. PATENT DOCUMENTS

| | | | | |
|---|---|---|---|---|
| 6,239,077 | B1 | 5/2001 | Andoh et al. | 504/312 |
| 7,052,707 | B2 | 5/2006 | Ducray et al. | 424/405 |
| 7,446,219 | B2 | 11/2008 | Ducray et al. | 558/391 |
| 2005/0033081 | A1 | 2/2005 | Ducray et al. | 558/392 |
| 2005/0059736 | A1 | 3/2005 | Ducray et al. | 514/521 |
| 2005/0203148 | A1 | 9/2005 | Ducray et al. | 514/345 |
| 2005/0203178 | A1 | 9/2005 | Ducray et al. | 514/521 |
| 2005/0272935 | A1 | 12/2005 | Ducray et al. | 548/257 |
| 2006/0025466 | A1 | 2/2006 | Ducray et al. | 514/406 |

FOREIGN PATENT DOCUMENTS

| | | |
|---|---|---|
| EP | 0953565 A2 | 11/1999 |
| EP | 1445251 A1 | 8/2004 |
| EP | 1445251 A9 | 8/2004 |
| WO | WO 02/049641 A2 | 6/2002 |
| WO | WO 02/50052 A1 | 6/2002 |
| WO | WO 02/060257 A1 | 8/2002 |
| WO | WO 02/092552 A3 | 11/2002 |
| WO | WO 02/102155 A1 | 12/2002 |
| WO | WO 03/031393 A2 | 4/2003 |
| WO | WO 03/031394 A1 | 4/2003 |
| WO | WO 03/042184 A1 | 5/2003 |
| WO | WO 03/048112 A1 | 6/2003 |
| WO | WO 03/059868 A1 | 7/2003 |
| WO | WO 03/080577 A2 | 10/2003 |
| WO | WO 03/097036 | * 11/2003 |
| WO | WO 03/097036 A1 | 11/2003 |
| WO | WO 03/097585 A2 | 11/2003 |
| WO | WO 03/104187 A1 | 12/2003 |
| WO | WO 03/104202 A1 | 12/2003 |
| WO | WO2004/000793 A2 | 12/2003 |
| WO | WO2004/000798 A1 | 12/2003 |
| WO | WO2004/024704 A1 | 3/2004 |
| WO | WO2005/044784 A1 | 5/2005 |
| WO | WO2005/058802 A1 | 6/2005 |
| WO | WO2005/121075 A1 | 12/2005 |
| WO | WO2006/043654 A1 | 4/2006 |
| WO | WO2006/050887 A1 | 5/2006 |
| WO | WO2007/017088 A1 | 2/2007 |
| WO | WO2008/062005 A1 | 5/2008 |
| WO | WO2008/064891 A1 | 6/2008 |
| WO | WO2008/096231 A1 | 8/2008 |
| WO | WO2008/096232 A1 | 8/2008 |
| WO | WO2008/144275 A1 | 11/2008 |

OTHER PUBLICATIONS

"Efficacy of the Amino-acetonitrile Derivative, Monepantel, Against Experimental and Natural Adult Stage Gastro-Intestinal Nematode Infections in Sheep," Sager et al, Veterinary Parasitology, 2009, 159, 49-54. Published Jan. 22, 2009.

"Pharmacokinetics of Monepantel and Its Sulfone Metabolite, Monepantel Sulfone, After Intravenous and Oral Administration in Sheep," D. Karadzovska et al., J. Vet Pharmacol. Therap., 2009, 32, 359-367. Published on-line May 6, 2009.

(Continued)

*Primary Examiner* — Joseph Kosack
*Assistant Examiner* — Alicia L Otton
(74) *Attorney, Agent, or Firm* — Judy Jarecki-Black; John Ezcurra; Merial Limited

(57) ABSTRACT

The present invention relates to novel thioamide derivatives of formula (I) and formula (Ia):

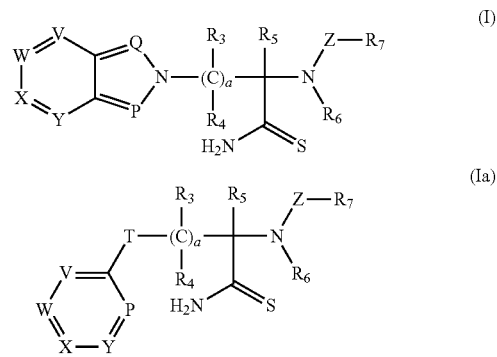

wherein, $R_3$, $R_4$, $R_5$, $R_6$, $R_7$, P, Q, T, V, W, X, Y, Z, a, m and n are as defined in the description, compositions thereof, processes for their preparation and their uses as pesticides.

24 Claims, No Drawings

OTHER PUBLICATIONS

"A New Class of Anthelmintics Effective Against drug-Resistant Nematodes," R. Kaminsky et al., Nature, 2008, 452 (13), 176-181.

"Identification of the Amino-Acetonitrile Derivative Monepantel (AAD 1566) As a New Anthelmintic Drug Development Candidate," R. Kaminsky et al., Parasitol Res., 2008, 103,931.

"Dose Determination Studies for Monepantel, an Amino-Acetonitrile Derivative, Against Fourth Stage Gastro-Intestinal Nematode Larvae Infecting Sheep," B.C. Hosking et al., Veterinary Parasitology, 2008, 157, 72-80.

"Discovery of Amino-Acetonitrile Derivatives, a New Class of Synthetic Anthelmintic Compounds," P. Ducray et al., Bioorganic & Medicinal Chemistry Letters, 2008, 18, 2935-2938.

"Simple Microwave-Assisted Method for the Synthesis of Primary Thioamides from Nitriles," M.C. Bagley et al., Synlett, 2004, 14, 2615-2617.

* cited by examiner

THIOAMIDE COMPOUNDS, METHOD OF MAKING AND METHOD OF USING THEREOF

INCORPORATION BY REFERENCE

This application is a divisional of U.S. patent application Ser. No. 12/582,486, filed Oct. 20, 2009, now U.S. Pat. No. 7,964,621 which claims the benefit of U.S. Provisional Application No. 61/107,114, filed Oct. 21, 2008, which is incorporated herein by reference in its entirety.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

FIELD OF THE INVENTION

The present invention relates to novel thioamide derivatives of formula (I) and (Ia):

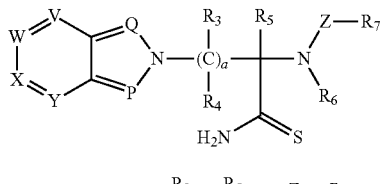

(I)

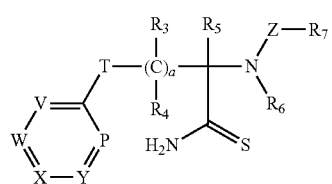

(Ia)

wherein, $R_3$, $R_4$, $R_5$, $R_6$, $R_7$, P, Q, T, V, W, X, Y, Z, a, m and n are as defined in the description, compositions thereof, processes for their preparation and their uses as pesticides.

BACKGROUND OF THE INVENTION

The control of parasites, particularly endoparasites which parasitize animals, by means of active material having a cyanoethylamide group has been described by many patents or patent application such as International Patent Publications No. WO 2002/049641, WO 2003/097036, WO 2003/097585, WO 2003/104187, WO 2004/000793, WO 2005/044784, WO 2005/05802, WO 2005/121075 and WO 2006/043654 as well as in EP 953565 (U.S. Pat. No. 6,239,077) and EP 1445251.

Novel aryl-azol-2-yl-cyanoethylamide derivatives of the formula:

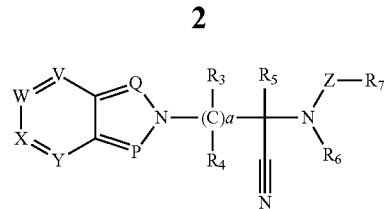

are described in US 2003/0312272 A1 to Soil et al., which is hereby incorporated by reference in.

However, none of the foregoing publications describe the compounds of formula (I) or formula (Ia), the method of making or the method of using possess activity as pesticides, particularly for controlling endoparasitic pests in animals.

OBJECTS AND SUMMARY OF THE INVENTION

The present invention relates to novel thioamide derivatives of formula (I) and (Ia):

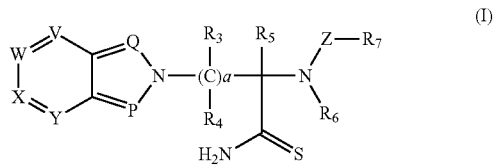

(I)

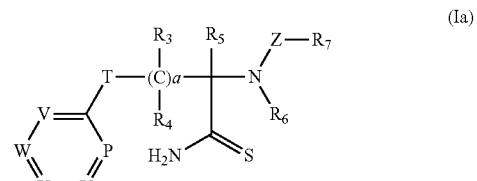

(Ia)

wherein:

$R_1$, $R_2$, $R_8$, $R_9$, $R_{10}$ and $R_{11}$, independently of one another, are hydrogen, cyano, nitro, halogen, alkyl, cycloalkyl, haloalkyl, alkylthio, haloalkylthio, alkylsulfinyl, haloalkylsulfinyl, alkylsulfonyl, haloalkylsulfonyl, $SF_5$, arylthio, alkoxy, cycloalkyloxy, haloalkoxy, alkylcarbonyl, haloalkylcarbonyl, alkylsulfinyl, haloalkylsulfinyl, alkylsulfonyl, alkylamino, di(alkyl)amino, unsubstituted or substituted aryl, unsubstituted or substituted heteroaryl, or unsubstituted or substituted phenoxy, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, or $SF_5$;

$R_3$, $R_4$ and $R_5$, independently of one another, are hydrogen, halogen, alkyl, haloalkyl; unsubstituted or substituted cycloalkyl, wherein the substituents may each be independent of one another and are selected from the group consisting of halogen and alkyl; unsubstituted or substituted aryl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, $SF_5$, alkylamino, di(alkyl)amino; or $R_4$ and $R_5$ together with the carbon to which they are attached form a cycloalkyl ring;

$R_6$ is hydrogen, alkyl, alkoxyalkyl, alkylcarbonyl, alkylthiocarbonyl or unsubstituted or substituted benzyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, $SF_5$, alkylamino, di(alkyl)amino;

$R_7$ is hydrogen, alkyl, alkoxyalkyl, alkylcarbonyl, alkylthiocarbonyl, unsubstituted or substituted aryl, including phenyl and naphthyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, $SF_5$, alkylamino, di(alkyl)amino; unsubstituted or substituted heteroaryl, including quinolyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, $SF_5$, alkylamino, di(alkyl)amino;

P is C—$R_1$ or N;
Q is C—$R_2$ or N;
V is C—$R_8$ or N;
W is C—$R_8$ or N;
X is C—$R_{18}$ or N;
Y is C—$R_{11}$ or N;
T is O, S or NH;
Z is a direct bond, C(O), C(S) or $S(O)_p$;
a is 1, 2 or 3; and
p is 1 or 2.

It is an object of the present invention to provide new pesticidal compounds of the thioamide derivatives of formula (I) and (Ia) together with processes for their preparation.

A second object of the present invention is to provide pesticidal compositions and pesticidal methods of use of the pesticidal thioamide derivatives of formula (I) and (Ia) in the field of pest control which are well tolerated by warm-blooded species, fish and plants, including in particular for controlling endo- and ectoparasites which parasitize animals.

Another object of the present invention is to provide compounds with high activity and improved safety to the user and the environment, which are obtained by optimization of chemical, physical and biological properties such as solubility, melting point, stability, electronic and steric parameters, and the like.

For the purposes of this application, unless otherwise stated in the specification, the following terms have the definitions cited below:

(1) Alkyl refers to both straight and branched carbon chains; references to individual alkyl groups are specific for the straight chain (e.g. butyl=n-butyl). In one embodiment of alkyl, the number of carbons atoms is 1-20, in another embodiment of alkyl, the number of carbon atoms is 1-8 carbon atoms and in yet another embodiment of alkyl, the number of carbon atoms is 1-4 carbon atoms. Other ranges of carbon numbers are also contemplated depending on the location of the alkyl moiety on the molecule;

(2) Alkenyl refers to both straight and branched carbon chains which have at least one carbon-carbon double bond. In one embodiment of alkenyl, the number of double bonds is 1-3; in another embodiment of alkenyl, the number of double bonds is one. In one embodiment of alkenyl, the number of carbons atoms is 2-20, in another embodiment of alkenyl, the number of carbon atoms is 2-8 and in yet another embodiment of alkenyl, the number of carbon atoms is 2-4. Other ranges of carbon-carbon double bonds and carbon numbers are also contemplated depending on the location of the alkenyl moiety on the molecule;

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in another embodiment of alkynyl, the number of carbon atoms is 2-8 and in yet another embodiment of alkynyl, the number of carbon atoms is 2-4. Other ranges of carbon-carbon double bonds and carbon numbers are also contemplated depending on the location of the alkenyl moiety on the molecule;

(4) Aryl refers to a $C_6$-$C_{14}$ aromatic carbocyclic ring structure having a single ring or multiple fused rings. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)amino, di(alkynyl)amino, or $SF_5$.

(5) Alkoxy refers to —O-alkyl, wherein alkyl is as defined in (1);

(6) Alkanoyl refers to formyl (—C(=O)H) and —C(=O)-alkyl, wherein alkyl is as defined in (1);

(7) Alkanoyloxy refers to —O—C(=O)-alkyl, wherein alkanoyl is as defined in (6);

(8) Alkanoylamino refers to —$NH_2$—C(=O)-alkyl, wherein alkanoyl is as defined in (6) and the amino ($NH_2$) moiety can be substituted by alkyl as defined in (1);

(9) Aminocarbonyl refers to —$NH_2$—C(=O), wherein the amino ($NH_2$) moiety can be substituted by alkyl as defined in (1);

(10) Alkoxycarbonyl refers to —C(=O)—O-alkyl, wherein alkoxy is as defined in (5);

(11) Alkenoyl refers to —C(=O)-alkenyl, wherein alkenyl is as defined in (2);

(12) Alkynoyl refers to —C(=O)-alkynyl, wherein alkynyl is as defined in (3);

(13) Aroyl refers to —C(=O)-aryl, wherein aryl is as defined above;

(14) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(15) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$));

(16) Heterocycle, heterocyclic or heterocyclo refer to fully saturated or unsaturated, cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(17) Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thiophenyl, furyl, imidazolyl, oxazolyl, isoxazolyl, isothiazolyl, pyrazolyl, benzofuranyl, and benzothiophenyl. Heteroaryl rings may be unsubstituted or substituted by one or more moieties as described for aryl above.

Exemplary monocyclic heterocyclic or heteroaryl groups also include pyrrolidinyl, pyrrolyl, pyrazolyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic or heteroaryl groups include indolyl, benzothiazolyl, benzoxazolyl, benzodioxolyl, benzothienyl, quinuclidinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic or heteroaryl groups include carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means a arylazol-2-yl-methylthiamide amido compound of the invention.

The compounds of the invention also are intended to encompass salt forms, racemic mixtures, specific stereoisomers, crystalline and amorphous forms of the compound.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

DETAILED DESCRIPTION OF THE INVENTION

A first aspect of the invention provides novel thioamide derivatives of formula (I) and (Ia):

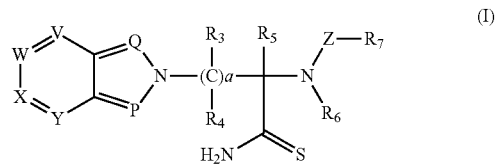

(I)

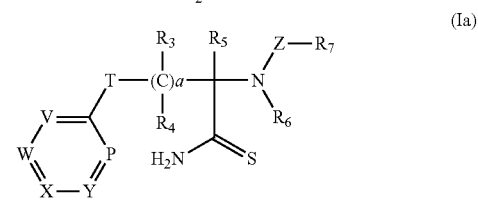

(Ia)

wherein $R_1$, $R_2$, $R_8$, $R_9$, $R_{10}$ and $R_{11}$, independently of one another, are hydrogen, cyano, nitro, halogen, $C_1$-$C_6$-alkyl, $C_3$-$C_7$-cycloalkyl, halo-$C_1$-$C_6$-alkyl, $C_1$-$C_6$-alkylthio, halo $C_1$-$C_6$-alkylthio, $C_1$-$C_6$-alkylsulfinyl, halo $C_1$-$C_6$-alkylsulfinyl, $C_1$-$C_6$-alkylsulfonyl, halo $C_1$-$C_6$-alkylsulfonyl, SF$_5$, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, unsubstituted or substituted aryl, or unsubstituted or substituted aryloxy including phenoxy, or unsubstituted or substituted heteroaryl, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, SF$_5$, and methylthioamino;

$R_3$, $R_4$ and $R_5$, independently of one another, are hydrogen, halogen, $C_1$-$C_6$-alkyl, halo-$C_1$-$C_6$-alkyl; $C_3$-$C_7$-cycloalkyl that is either unsubstituted or substituted, whereby the substituents may each be independent of one another and are selected from the group consisting of halogen and $C_1$-$C_6$-alkyl; and aryl that is either unsubstituted or substituted, whereby the substituents may each be independent of one another and are selected from the group consisting of cyano, nitro, halogen, $C_1$-$C_6$-alkyl, halo-$C_1$-$C_6$-alkyl, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, $C_1$-$C_6$-alkylamino, and di($C_1$-$C_6$-alkyl)amino;

or $R_4$ and $R_5$ together signify $C_2$-$C_6$-alkylene;

$R_6$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or benzyl that is either unsubstituted or substituted, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, $C_1$-$C_6$-alkylamino, and di($C_1$-$C_6$-alkyl)amino;

$R_7$ is hydrogen, $C_1$-$C_6$-alkyl, $C_1$-$C_6$-alkoxy-$C_1$-$C_6$-alkylcarbonyl, $C_1$-$C_6$-alkylthiocarbonyl or aryl, including phenyl and naphthyl, that is either unsubstituted or substituted, whereby the substituents may each be independent of one another and are selected from the group consisting of cyano, nitro, halogen, $C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_8$-alkyl)amino; heteroaryl, including quinolyl, that is either unsubstituted or substituted, whereby the substituents may each be independent of one another and are selected from the group consisting of cyano, nitro, halogen, $C_1$-$C_6$-alkyl, halo-$C_1$-$C_6$-alkyl, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_8$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_8$-alkyl)amino;

P is C—$R_1$ or N;
Q is C—$R_2$ or N;
V is C—$R_8$ or N;
W is C—$R_9$ or N;
X is C—$R_{10}$ or N;
Y is C—$R_{11}$ or N;
Z is a direct bond, C(O), C(S) or S(O)$_p$;
T is independently O, S or NH;
a is 1, 2 or 3; and
p is 1 or 2.

In one embodiment of the first aspect of the invention, compounds of formula (I) above are compounds wherein:

P and Q are N;
V is C—$R_8$;
W is C—$R_9$;
X is C—$R_{10}$;
Y is C—$R_{11}$;

$R_8$, $R_9$, $R_{10}$ and $R_{11}$, independently of one another, are cyano, nitro, halogen, $C_1$-$C_6$-alkyl, $C_3$-$C_7$-cycloalkyl, $C_1$-$C_6$-alkylthio, halo $C_1$-$C_6$-alkylthio, $C_1$-$C_6$-alkylsulfinyl, halo $C_1$-$C_6$-alkylsulfinyl, $C_1$-$C_6$-alkylsulfonyl, halo $C_1$-$C_6$-alkylsulfonyl, $SF_5$, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$- alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl) amino, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, and methylthioamino;

$R_3$, $R_4$ and $R_6$ are H;
$R_5$ is methyl or $C_1$-$C_3$-alkyl;

$R_7$ is unsubstituted or substituted phenyl wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino; unsubstituted or substituted heteroaryl, wherein the substituents may each be independent of one another and are selected from the group consisting of cyano, nitro, halogen, $C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino; or unsubstituted or substituted naphthyl or quinolyl, wherein the substituents may each be independent of one another and are selected from the group consisting of cyano, nitro, halogen, $C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, and di($C_1$-$C_6$-alkyl)amino;

Z is a direct bond, C(O), C(S) or S(O)$_p$; and
a is 1.

In yet another embodiment of the first aspect of the invention, compounds of formula (I) or (Ia) above are compounds wherein:

P and Q are N;
V is C—$R_8$;
W is C—$R_9$;
X is C—$R_{10}$;
Y is C—$R_{11}$;

$R_8$, $R_9$, $R_{10}$ and $R_{11}$, independently of one another, are cyano, nitro, halogen, $C_1$-$C_6$-alkyl, $C_3$-$C_7$-cycloalkyl, $C_1$-$C_6$-alkylthio, halo $C_1$-$C_6$-alkylthio, $C_1$-$C_6$-alkylsulfinyl, halo $C_1$-$C_6$-alkylsulfinyl, $C_1$-$C_6$-alkylsulfonyl, halo $C_1$-$C_6$-alkylsulfonyl, $SF_5$, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, and methylthioamino;

$R_3$, $R_4$ and $R_6$ are H;
$R_5$ is methyl or $C_1$-$C_3$-alkyl;

$R_7$ is unsubstituted or substituted phenyl wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-

$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino; unsubstituted or substituted heteroaryl, wherein the substituents may each be independent of one another and are selected
from the group consisting of cyano, nitro, halogen, $C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino;
Z is C(O);
T is independently O, S or NH; and
a is 1.

In still another embodiment of the first aspect of the invention, compounds of formula (I) or (Ia) above are compounds wherein:
P and Q is N;
V is C—$R_8$;
W is C—$R_9$;
X is C—$R_{10}$;
Y is C—$R_{11}$;
$R_8$, $R_9$, $R_{10}$ and $R_{11}$, independently of one another, are cyano, nitro, halogen, $C_1$-$C_6$-alkyl, $C_3$-$C_7$-cycloalkyl, halo-$C_1$-$C_6$alkyl, $C_1$-$C_6$-alkylthio, halo $C_1$-$C_6$-alkylthio, $C_1$-$C_6$-alkylsulfinyl, halo $C_1$-$C_6$-alkylsulfinyl, $C_1$-$C_6$-alkylsulfonyl, halo $C_1$-$C_6$-alkylsulfonyl, $SF_5$, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$alkylsulfinyl, halo-$C_1$-$C_6$-alkylsulfinyl, $C_1$-$C_6$-alkylsulfonyl, halo-$C_1$-$C_6$-alkylsulfonyl, $SF_5$, and methylthioamino;
$R_3$, $R_4$ and $R_6$ are H;
$R_5$ is methyl;
$R_7$ is unsubstituted or substituted phenyl wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino; unsubstituted or substituted heteroaryl, wherein the substituents may each be independent of one another and are selected from the group consisting of cyano, nitro, halogen, $C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino;
Z is C(O)
a is 1;
m and n are independently 0 or 1.

In still another embodiment of the first aspect of the invention, compounds of formula (I) or (Ia) above are compounds wherein:
$R_1$, $R_2$, $R_8$, $R_9$, $R_{10}$ and $R_{11}$, independently of one another, are hydrogen, cyano, halogen, $C_1$-$C_6$-alkyl, halomethyl or methylthioamino;
$R_3$, $R_4$ and $R_6$ are H;
$R_5$ is methyl or $C_1$-$C_3$-alkyl;
P is C—$R_1$ or N;
Q is C—$R_2$ or N;
V is C—$R_8$ or N;
W is C—$R_8$;
X is C—$R_{10}$;
Y is C—$R_{11}$ or N;
T is O or S;
Z is C(O); and
a is 1.

In still another embodiment of the first aspect of the invention, compounds of formula (I) above are compounds wherein:
$R_1$, $R_2$, $R_8$, $R_9$, $R_{10}$ and $R_{11}$, independently of one another, are hydrogen, cyano, chloro, bromo, methyl or trifluoromethyl;
$R_3$, $R_4$ and $R_6$ is H;
$R_5$ is methyl;
P is C—$R_1$ or N;
Q is C—$R_2$ or N;
V is C—$R_8$ or N;
W is C—$R_8$;
X is C—$R_{10}$;
Y is C—$R_{11}$ or N;
Z is C(O);
$R_7$ is a substituted phenyl wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, and
a is 1.

In still another embodiment of the first aspect of the invention, compounds of formula (I) above are compounds wherein:
$R_8$, $R_9$, $R_{10}$ and $R_{11}$, independently of one another, are hydrogen, cyano, chloro, bromo, methyl or trifluoromethyl;
$R_3$, $R_4$ and $R_6$ is H;
$R_5$ is methyl;
P is N;
Q is N;
V is C—$R_8$;
W is C—$R_8$;
X is C—$R_{10}$;
Y is C—$R_{11}$;
Z is C(O);
$R_7$ is a substituted phenyl wherein the substituents may each be independent of one another and are selected from the group consisting of halogen, $C_1$-$C_6$-alkylthio, halo-$C_1$-$C_6$-alkylthio, $C_1$-$C_6$-alkoxy, and halo-$C_1$-$C_6$-alkoxy, and
a is 1.

In still another embodiment of the first aspect of the invention, compounds of formula (I) above are compounds wherein:
$R_8$, $R_9$, $R_{10}$ and $R_{11}$, independently of one another, are hydrogen, cyano, chloro, bromo, methyl, or trifluoromethyl;
$R_3$, $R_4$ and $R_6$ is H;
$R_5$ is methyl;
P is N;
Q is N;
V is C—$R_8$;
W is C—$R_9$;
X is C—$R_{10}$;

Y is C—$R_{11}$;
Z is C(O);
$R_7$ is a substituted phenyl wherein the substituents may each be independent of one another and are selected from the group consisting of halo-$C_1$-$C_6$-alkylthio and halo-$C_1$-$C_6$-alkoxy, and
a is 1.

In another embodiment of the first aspect of the invention, compounds of formula (I) above are compounds wherein:
$R_9$, $R_{10}$ and $R_{11}$, independently of one another, are hydrogen, cyano, chloro, bromo, methyl or trifluoromethyl;
$R_3$, $R_4$ and $R_6$ are H;
$R_2$ is H, chloro, bromo or $C_1$-$C_6$-alkoxy;
$R_5$ is methyl;
P is N;
Q is C—$R_2$;
V is N;
W is C—$R_9$;
X is C—$R_{10}$;
Y is C—$R_{11}$;
Z is C(O);
$R_7$ is a substituted phenyl wherein the substituents may each be independent of one another and are selected from the group consisting of halo-$C_1$-$C_6$-alkylthio and halo-$C_1$-$C_6$-alkoxy, and
a is 1.

In still another embodiment of the first aspect of the invention, compounds of formula (I) above are compounds wherein:
$R_8$, $R_9$, $R_{10}$ and $R_{11}$, independently of one another, are hydrogen, chloro, bromo, methyl or trifluoromethyl;
$R_3$, $R_4$ and $R_6$ is H;
$R_2$ is H, chloro, bromo or $C_1$-$C_6$-alkoxy;
$R_5$ is methyl;
P is N;
Q is C—$R_2$;
V is C—$R_8$;
W is C—$R_9$;
X is C—$R_{10}$;
Y is C—$R_{11}$;
Z is C(O);
$R_7$ is a substituted phenyl wherein the substituents may each be independent of one another and are selected from the group consisting of halo-$C_1$-$C_6$-alkylthio and halo-$C_1$-$C_6$-alkoxy, and
a is 1.

In still another embodiment of the first aspect of the invention, compounds of formula (I) above are compounds wherein:
$R_9$, $R_{10}$ and $R_{11}$, independently of one another, are hydrogen, cyano, chloro, bromo, methyl or trifluoromethyl;
$R_3$, $R_4$ and $R_6$ is H;
$R_5$ is methyl;
P is N;
Q is N;
V is C—$R_8$;
W is C—$R_9$;
X is C—$R_{10}$;
Y is C—$R_{11}$;
Z is C(O);
$R_7$ is a substituted phenyl wherein the substituents may each be independent of one another and are selected from the group consisting of halo-$C_1$-$C_6$-alkylthio and halo-$C_1$-$C_6$-alkoxy, and
a is 1.

In another embodiment of the first aspect of the invention, compounds of formula (I) above are compounds wherein:
$R_9$, $R_{10}$ and $R_{11}$, independently of one another, are hydrogen, chloro, bromo or methyl;
$R_3$, $R_4$ and $R_6$ are H;
$R_2$ is H, chloro, bromo or methoxy;
$R_5$ is methyl;
P is N;
Q is C—$R_2$;
V is N;
W is C—$R_9$;
X is C—$R_{10}$;
Y is C—$R_{11}$;
Z is C(O);
$R_7$ is a substituted phenyl wherein the substituents may each be independent of one another and are selected from the group consisting of halo-$C_1$-$C_6$-alkylthio and halo-$C_1$-$C_6$-alkoxy, and
a is 1.

In still another embodiment of the first aspect of the invention, compounds of formula (I) above are compounds wherein:
$R_8$, $R_9$, $R_{10}$ and $R_{11}$, independently of one another, are hydrogen, chloro, bromo, methyl or trifluoromethyl;
$R_3$, $R_4$ and $R_6$ is H;
$R_2$ is H, chloro, bromo, methoxy, ethoxy, propoxy or butoxy;
$R_5$ is methyl;
P is N;
Q is C—$R_2$;
V is C—$R_9$;
W is C—$R_9$;
X is C—$R_{10}$;
Y is C—$R_{11}$;
Z is C(O);
$R_7$ is a substituted phenyl wherein the substituents may each be independent of one another and are selected from the group consisting of halo-$C_1$-$C_6$-alkylthio and halo-$C_1$-$C_6$-alkoxy, and
a is 1.

In still another embodiment of the first aspect of the invention, compounds of formula (Ia) above are compounds wherein:
$R_1$, $R_8$, $R_9$, $R_{10}$ and $R_{11}$, independently of one another, are hydrogen, cyano, chloro, triifluoromethyl or methylamino;
$R_3$, $R_4$ and $R_6$ is H;
$R_5$ is methyl;
P is C—$R_1$ or N;
V is C—$R_9$ or N;
W is C—$R_9$;
X is C—$R_{10}$;
Y is C—$R_{11}$ or N;
Z is C(O);
T is O;
$R_7$ is a substituted phenyl wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, and
a is 1.

In still another embodiment of the first aspect of the invention, compounds of formula (Ia) above are compounds wherein:
$R_8$, $R_9$, $R_{10}$ and $R_{11}$, independently of one another, are hydrogen, cyano, chloro, trifluoromethyl or methylthioamino;
$R_3$, $R_4$ and $R_6$ is H;
$R_5$ is methyl;
P is N;
V is C—$R_8$;

W is C—R$_9$;
X is C—R$_{10}$;
Y is C—R$_{11}$;
Z is C(O);
T is O;
R$_7$ is a substituted phenyl wherein the substituents may each be independent of one another and are selected from the group consisting of halogen, C$_1$-C$_6$-alkylthio, halo-C$_1$-C$_6$-alkylthio, C$_1$-C$_6$-alkoxy, and halo-C$_1$-C$_6$-alkoxy, and
a is 1.

In still another embodiment of the first aspect of the invention, compounds of formula (Ia) above are compounds wherein:
R$_8$, R$_9$, R$_{10}$ and R$_{11}$, independently of one another, are hydrogen, cyano, chloro, trifluoromethyl or methylthioamino;
R$_3$, R$_4$ and R$_6$ is H;
R$_5$ is methyl;
P is N;
V is C—R$_8$;
W is C—R$_9$;
X is C—R$_{10}$;
Y is C—R$_{11}$;
Z is C(O);
T is O;
R$_7$ is a substituted phenyl wherein the substituents may each be independent of one another and are selected from the group consisting of halo-C$_1$-C$_6$-alkylthio and halo-C$_1$-C$_6$-alkoxy, and
a is 1.

Tables 1, 2 and 3 below provide additional particularly preferred compounds of the invention of formula (Ib), (Ic) and (Id) that are encompassed by formula (I).

TABLE 1

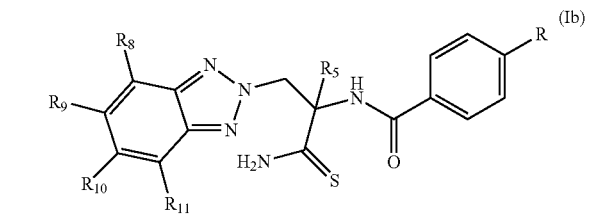
(Ib)

V = C—R$_8$; W = C—R$_9$; X = C—R$_{10}$; Y = C—R$_{11}$;
Q = P = N;
R$_3$ = R$_4$ = R$_6$ = H; a = 1; R$_5$ = CH$_3$;
Z = C(O); R$_7$ = p-phenyl-R

| Compound # | R | R$_5$ | R$_8$ | R$_9$ | R$_{10}$ | R$_{11}$ |
|---|---|---|---|---|---|---|
| 1.001 | OCF$_3$ | Me | H | Cl | H | H |
| 1.002 | CF$_3$ | Me | H | Cl | H | H |
| 1.003 | SCF$_3$ | Me | H | Cl | H | H |
| 1.004 | OCF$_3$ | Me | H | H | H | H |
| 1.005 | SCF$_3$ | Me | H | H | H | H |
| 1.006 | OCF$_3$ | Me | H | Me | H | H |
| 1.007 | SCF$_3$ | Me | H | Me | H | H |
| 1.008 | OCF$_3$ | Me | H | CF$_3$ | H | H |
| 1.009 | SCF$_3$ | Me | H | CF$_3$ | H | H |
| 1.010 | OCF$_3$ | Me | H | Cl | Cl | H |
| 1.011 | SCF$_3$ | Me | H | Cl | Cl | H |
| 1.012 | OCF$_3$ | Me | Cl | H | Cl | H |
| 1.013 | SCF$_3$ | Me | Cl | H | Cl | H |
| 1.014 | OCF$_3$ | Me | Cl | H | CF$_3$ | H |
| 1.015 | SCF$_3$ | Me | Cl | H | CF$_3$ | H |
| 1.016 | OCF$_3$ | Me | H | CN | H | H |
| 1.017 | SCF$_3$ | Me | H | CN | H | H |
| 1.018 | OCF$_3$ | Me | CF$_3$ | H | CF$_3$ | H |
| 1.019 | SCF$_3$ | Me | CF$_3$ | H | CF$_3$ | H |
| 1.020 | OCF$_3$ | Me | H | Br | H | H |

TABLE 1-continued

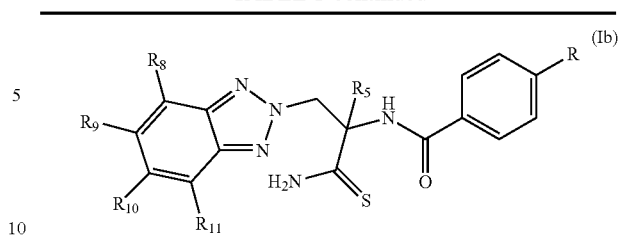
(Ib)

V = C—R$_8$; W = C—R$_9$; X = C—R$_{10}$; Y = C—R$_{11}$;
Q = P = N;
R$_3$ = R$_4$ = R$_6$ = H; a = 1; R$_5$ = CH$_3$;
Z = C(O); R$_7$ = p-phenyl-R

| Compound # | R | R$_5$ | R$_8$ | R$_9$ | R$_{10}$ | R$_{11}$ |
|---|---|---|---|---|---|---|
| 1.021 | SCF$_3$ | Me | H | Br | H | H |
| 1.022 | SOCF$_3$ | Me | H | CN | H | H |
| 1.023 | SOCF$_3$ | Me | Cl | H | CF$_3$ | H |
| 1.024 | SOCF$_3$ | Me | Cl | H | Cl | H |
| 1.025 | SO$_2$CF$_3$ | Me | Cl | H | Cl | H |
| 1.026 | SO$_2$CF$_3$ | Me | H | CF$_3$ | H | H |
| 1.027 | SO$_2$CF$_3$ | Me | H | CN | H | H |
| 1.028 | SO$_2$CF$_3$ | Me | Cl | H | CF$_3$ | H |
| 1.029 | SO$_2$CF$_3$ | Me | H | H | H | H |
| 1.030 | SO$_2$CF$_3$ | Me | H | Me | H | H |
| 1.031 | SO$_2$CF$_3$ | Me | H | Cl | H | H |
| 1.032 | OPh | Me | H | Cl | H | H |
| 1.033 | OCF$_3$ | Me | Me | H | Cl | H |
| 1.034 | SCF$_3$ | Me | Me | H | Cl | H |
| 1.035 | OCF$_3$ | Me | H | OCF$_3$ | H | H |
| 1.036 | SCF$_3$ | Me | H | OCF$_3$ | H | H |
| 1.037 | OCF$_3$ | Me | CF$_3$ | H | Cl | H |
| 1.038 | SCF$_3$ | Me | CF$_3$ | H | Cl | H |
| 1.039 | OPh | Me | Me | H | Cl | H |
| 1.040 | OCF$_3$ | Me | H | Cl | Me | H |
| 1.041 | SCF$_3$ | Me | H | Cl | Me | H |
| 1.042 | OPh | Me | CF$_3$ | H | Cl | H |
| 1.043 | OCF$_3$ | Me | H | Cl | H | H |
| 1.044 | SCF$_3$ | Me | H | Cl | H | H |
| 1.045 | OPh | Me | H | Cl | H | H |
| 1.046 | Ph | Me | H | Cl | H | H |
| 1.047 | OCF$_3$ | Et | H | Cl | H | H |
| 1.048 | SCF$_3$ | Et | H | Cl | H | H |
| 1.049 | OCF$_3$ | CH$_2$CH(CH$_3$)$_2$ | H | Cl | H | H |
| 1.050 | SCF$_3$ | CH$_2$CH(CH$_3$)$_2$ | H | Cl | H | H |
| 1.051 | OCF$_3$ | t-Bu | H | Cl | H | H |
| 1.052 | SCF$_3$ | t-Bu | H | Cl | H | H |
| 1.053 | t-Bu | Me | Cl | H | Cl | H |
| 1.054 | OCF$_3$ | Me | CN | H | CF$_3$ | H |
| 1.055 | SCF$_3$ | Me | CN | H | CF$_3$ | H |
| 1.056 | OCF$_3$ | Me | CF$_3$ | H | CN | H |
| 1.057 | OCF$_3$ | Me | Br | Cl | H | H |
| 1.058 | OCF$_3$ | CH$_2$OH | H | Cl | H | H |
| 1.059 | SCF$_3$ | CH$_2$OH | H | Cl | H | H |
| 1.060 | OCF$_3$ | Me | Br | H | Cl | H |
| 1.061 | OCF$_3$ | CH$_2$SMe | H | Cl | H | H |
| 1.062 | OCF$_3$ | CH$_2$OMe | H | Cl | H | H |
| 1.063 | OCF$_3$ | CHOSO$_2$Me | H | Cl | H | H |
| 1.064 | OCF$_3$ | Me | Cl | Cl | H | Cl |
| 1.065 | SCF$_3$ | Me | Cl | Cl | H | Cl |
| 1.066 | SCF$_3$ | Me | CF$_3$ | H | CN | H |
| 1.067 | OCF$_3$ | Me | CN | H | Cl | H |
| 1.068 | OCF$_3$ | Me | p-Ph—CF$_3$ | H | Cl | H |
| 1.069 | CHFCF$_3$ | Me | Cl | Cl | H | Cl |
| 1.070 | OCF$_3$ | Me | Cl | H | OMe | H |
| 1.071 | SCF$_3$ | Me | Cl | H | OMe | H |
| 1.072 | OCF$_3$ | Me | H | OMe | H | H |
| 1.073 | SCF$_3$ | Me | H | OMe | H | H |
| 1.074 | OCF$_3$ | Me | CH$_2$NH$_2$ | H | Cl | H |
| 1.075 | OCF$_3$ | Me | Vinyl | H | Cl | H |
| 1.076 | SCF$_3$ | Me | Vinyl | H | Cl | H |
| 1.077 | OCF$_3$ | Me | CH(OH)CH$_2$OH | H | Cl | H |
| 1.078 | OCF$_3$ | Me | CH(F)CH$_2$F | H | Cl | H |
| 1.079 | OCF$_3$ | Me | Formyl | H | Cl | H |
| 1.080 | OCF$_3$ | Me | CH$_2$NMe$_2$ | H | Cl | H |
| 1.081 | OCF$_3$ | Me | CH$_2$OH | H | Cl | H |
| 1.082 | OCF$_3$ | Me | CO$_2$H | H | Cl | H |

TABLE 1-continued

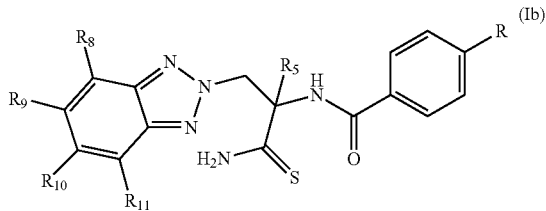
(Ib)

V = C—$R_8$; W = C—$R_9$; X = C—$R_{10}$; Y = C—$R_{11}$;
Q = P = N;
$R_3 = R_4 = R_6$ = H; a = 1; $R_5 = CH_3$;
Z = C(O); $R_7$ = p-phenyl-R

| Compound # | R | $R_5$ | $R_8$ | $R_9$ | $R_{10}$ | $R_{11}$ |
|---|---|---|---|---|---|---|
| 1.083 | $OCF_3$ | Me | Br | Cl | H | Br |
| 1.084 | $OCF_3$ | Me | $CO_2Me$ | H | Cl | H |
| 1.085 | $SCF_3$ | Me | Br | Cl | H | Br |
| 1.086 | $OCF_3$ | Me | Br | Cl | H | Cl |
| 1.087 | $SCF_3$ | Me | Br | Cl | H | Cl |
| 1.088 | $OCF_3$ | Me | Br | Cl | Br | Cl |
| 1.089 | $SCF_3$ | Me | Br | Cl | Br | Cl |
| 1.090 | $OCF_3$ | Me | F | Cl | H | Cl |
| 1.091 | $SCF_3$ | Me | F | Cl | H | Cl |
| 1.092 | $OCF_3$ | Me | Me | Cl | H | Me |
| 1.093 | $SCF_3$ | Me | Me | Cl | H | Me |
| 1.094 | $OCF_3$ | Me | F | Br | H | Me |
| 1.095 | $SCF_3$ | Me | F | Br | H | Me |

TABLE 2

(Ic)

V = C—$R_8$; W = C—$R_9$; X = C—$R_{10}$; Y = C—$R_{11}$;
Q = C—$R_2$; P = N;
$R_3 = R_4 = R_6$ = H; a = 1; $R_5 = CH_3$;
Z = C(O); $R_7$ = p-phenyl-R

| Compound # | R | $R_2$ | $R_8$ | $R_9$ | $R_{10}$ | $R_{11}$ |
|---|---|---|---|---|---|---|
| 2.001 | $OCF_3$ | H | H | $NO_2$ | H | H |
| 2.002 | $SCF_3$ | H | H | $NO_2$ | H | H |
| 2.003 | $OCF_3$ | H | H | Cl | H | Cl |
| 2.004 | OPh | H | H | Cl | H | Cl |
| 2.005 | $SCF_3$ | H | H | Cl | H | Cl |
| 2.006 | $OCF_3$ | H | H | Cl | H | Me |
| 2.007 | $SCF_3$ | H | H | Cl | H | Me |
| 2.008 | $OCF_3$ | OMe | H | H | Cl | H |
| 2.009 | $SCF_3$ | OMe | H | H | Cl | H |
| 2.010 | $OCF_3$ | Me | H | Cl | H | Cl |
| 2.011 | $SCF_3$ | Me | H | Cl | H | Cl |
| 2.012 | $OCF_3$ | OMe | H | Cl | H | H |
| 2.013 | $SCF_3$ | OMe | H | Cl | H | H |
| 2.014 | $OCF_3$ | OEt | H | Cl | H | H |
| 2.015 | $SCF_3$ | OEt | H | Cl | H | H |
| 2.016 | $OCF_3$ | OMe | H | H | H | H |
| 2.017 | $OCF_3$ | $O(CH_2)_2OMe$ | H | H | H | H |
| 2.018 | $OCF_3$ | $O(CH_2)_2NMe_2$ | H | H | Cl | H |
| 2.019 | $SCF_3$ | OMe | H | Cl | H | Cl |
| 2.020 | $OCF_3$ | OMe | H | Cl | H | Cl |
| 2.021 | $OCF_3$ | OMe | Cl | H | Cl | H |
| 2.022 | $SCF_3$ | OMe | Cl | H | Cl | H |
| 2.023 | $OCF_3$ | OMe | H | H | Br | H |
| 2.024 | $SCF_3$ | OMe | H | H | Br | H |
| 2.025 | $OCF_3$ | OMe | H | H | $CF_3$ | H |
| 2.026 | $SCF_3$ | OMe | H | H | $CF_3$ | H |

TABLE 2-continued (Ic)

V = C—$R_8$; W = C—$R_9$; X = C—$R_{10}$; Y = C—$R_{11}$;
Q = C—$R_2$; P = N;
$R_3 = R_4 = R_6$ = H; a = 1; $R_5 = CH_3$;
Z = C(O); $R_7$ = p-phenyl-R

| Compound # | R | $R_2$ | $R_8$ | $R_9$ | $R_{10}$ | $R_{11}$ |
|---|---|---|---|---|---|---|
| 2.027 | $OCF_3$ | OEt | H | H | Cl | H |
| 2.028 | $SCF_3$ | OEt | H | H | Cl | H |
| 2.029 | $OCF_3$ | O-n-Pr | H | H | Cl | H |
| 2.030 | $SCF_3$ | O-n-Pr | H | H | Cl | H |
| 2.031 | $OCF_3$ | O-n-Bu | H | H | Cl | H |
| 2.032 | $OCF_3$ | OMe | H | H | $CO_2Me$ | H |
| 2.033 | $OCF_3$ | OMe | H | H | $NO_2$ | H |
| 2.034 | $OCF_3$ | OMe | H | H | $NH_2$ | H |
| 2.035 | $OCF_3$ | OMe | H | H | NHAc | H |
| 2.036 | $OCF_3$ | OMe | H | H | $CONH_2$ | H |
| 2.037 | $OCF_3$ | H | H | H | Cl | H |
| 2.038 | $SCF_3$ | H | H | H | Cl | H |
| 2.039 | $OCF_3$ | Cl | H | H | Cl | Cl |
| 2.040 | $OCF_3$ | H | H | Cl | Cl | H |
| 2.041 | $SCF_3$ | H | H | Cl | Cl | H |
| 2.042 | $OCF_3$ | Br | H | H | Cl | H |
| 2.043 | $OCF_3$ | H | H | H | Cl | Br |
| 2.044 | $OCF_3$ | Cl | H | H | Cl | H |
| 2.045 | $OCF_3$ | H | H | H | Cl | Cl |
| 2.046 | $OCF_3$ | Br | H | H | Cl | Br |
| 2.047 | $OCF_3$ | H | H | Cl | H | Br |
| 2.048 | $OCF_3$ | H | H | Cl | H | Cl |
| 2.049 | $SCF_3$ | H | H | Cl | H | Cl |
| 2.050 | $OCF_3$ | Me | H | H | Cl | H |

TABLE 3

V = N; W = C—$R_9$; X = C—$R_{10}$; Y = C—$R_{11}$;
Q = C—$R_2$ where $R_2$ is as defined for formula (I) above; P = N;
$R_3 = R_4 = R_6$ = H; a = 1; $R_5 = CH_3$;
Z = C(O), $R_7$ = p-phenyl-R

| Compound # | R | Q | $R_9$ | $R_{10}$ | $R_{11}$ |
|---|---|---|---|---|---|
| 3.001 | $OCF_3$ | C—OMe | H | Cl | H |
| 3.002 | $SCF_3$ | C—OMe | H | Cl | H |
| 3.003 | $OCF_3$ | N | H | Br | Me |
| 3.004 | $SCF_3$ | N | H | Br | Me |
| 3.005 | $OCF_3$ | C—H | H | Cl | H |
| 3.006 | $SCF_3$ | C—H | H | Cl | H |
| 3.007 | $OCF_3$ | C—OMe | H | Br | Me |
| 3.008 | $OCF_3$ | C—OMe | H | Cl | Me |
| 3.009 | $OCF_3$ | C—H | H | Br | Me |
| 3.010 | $OCF_3$ | C—H | H | Cl | Me |
| 3.011 | $OCF_3$ | C—H | H | Br | H |
| 3.012 | $SCF_3$ | C—H | H | Br | H |
| 3.013 | $OCF_3$ | C—H | H | Cl | Cl |
| 3.014 | $SCF_3$ | C—H | H | Cl | Cl |
| 3.015 | $OCF_3$ | C—H | H | Br | Cl |
| 3.016 | $SCF_3$ | C—H | H | Br | Cl |
| 3.017 | $OCF_3$ | C—Cl | H | Cl | H |

TABLE 3-continued

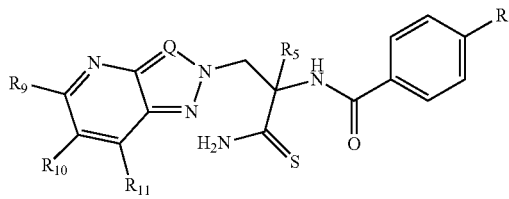

V = N; W = C—$R_9$; X = C—$R_{10}$; Y = C—$R_{11}$;
Q = C—$R_2$ where $R_2$ is as defined for formula (I) above; P = N;
$R_3 = R_4 = R_6$ = H; a = 1; $R_5$ = $CH_3$;
Z = C(O), $R_7$ = p-phenyl-R

| Compound # | R | Q | $R_9$ | $R_{10}$ | $R_{11}$ |
|---|---|---|---|---|---|
| 3.018 | $SCF_3$ | C—Cl | H | Cl | H |
| 3.019 | $OCF_3$ | C—Br | H | Cl | H |
| 3.020 | $SCF_3$ | C—Br | H | Cl | H |
| 3.021 | $OCF_3$ | C—H | H | Cl | Br |
| 3.022 | $SCF_3$ | C—H | H | Cl | Br |
| 3.023 | $SCF_3$ | C—H | H | Br | Me |

Formulations and Administration for Pharmaceutical/Veterinary Use

Another aspect of the invention is the formation of antiparasiticidal compositions which comprise the thioamide compounds of the invention. The composition of the invention can also be in a variety of forms which include, but are not limited to, oral formulations, injectable formulations, and topical, dermal or subdermal formulations.

The composition of the invention may be in a form suitable for oral use, for example, as baits (see, e.g., U.S. Pat. No. 4,564,631), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellu lose, sodium alginate, polyinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the compound(s) of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the 1-aryl-5-alkyl compound into the carrier by mixing;
(b) adding the fumed silica to the carrier containing the dissolved active compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste. The above steps are illustrative, but not limiting. For example, step (a) can be the last step.

In one embodiment of the formulation, the formulation is a paste containing a thioamide compound of the invention, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (polysorbate 80 or Tween 80), and polyoxamers (e.g., Pluronic L 81); an absorbent selected from the group consisting of magnesium carbonate, calcium carbonate, starch, and cellulose and its derivatives; and a colorant selected from the group consisting of titanium dioxide iron oxide, and FD&C Blue #1 Aluminum Lake.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringers solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions. Topical application of an inventive compound or of a composition including at least one inventive compound among active agent(s) therein, a spot-on composition, can allow for the inventive compound to be distributed through the glands (e.g. sebaceous glands) of the animal and/or allow active agent(s) to achieve a systemic effect (plasma concentration) or throughout the haircoat. When the compound is distributed throughout glands, the glands can act as a reservoir, whereby there can be a long-lasting, e.g. 1-2 months effect. Spot-on formulations are typically applied in a localized region which refers to an area other than the entire animal. In one embodiment of a localized region, the location is between the shoulders. In another embodiment of a localized region is a stripe, e.g. a stripe from head to tail of the animal.

Pour-on formulations are described in U.S. Pat. No. 6,010,710, incorporated herein by reference. The pour-on formulations are advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, mention may be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent will be added. One embodiment of the emollient and/or spreading and/or film-forming agent are those agents selected from the group consisting of:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+R'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the thioamide compound of formula (I) or (Ia) and its solubility in this solvent. It will be sought to have the lowest possible volume. The vehicle makes up the difference to 100%.

In one embodiment of the amount of emollient, the emollient is used in a proportion selected from the group consisting of from 0.1 to 10% and 0.25 to 5%, by volume.

In another embodiment of the invention, the composition can be in ready-to-use solution form as is described in U.S. Pat. No. 6,395,765, incorporated herein by reference. In addition to the thioamide compound of formula (I) or (Ia), the ready-to-use solution can contain a crystallization inhibitor, an organic solvent and an organic co-solvent.

In one embodiment of the amount of crystallization inhibitor, the crystallization inhibitor can be present in a proportion selected from the group consisting of about 1 to about 20% (w/v) and about 5 to about 15%. In another embodiment of the amount of crystallization inhibitor, the amount corresponds to the test in which 0.3 ml of a solution comprising 10% (w/v) of the thioamide compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystal.

The organic solvent has a dielectric constant of a range selected from the group consisting of between about 10 and 35 and between about 20 and 30, the content of this organic solvent in the overall composition representing the complement to 100% of the composition; and the organic co-solvent having a boiling point selected from the ranges consisting of below 100° C., and below 80° C., and having a dielectric constant of a range selected from the group consisting of between about 10 and 40 and between about 20 and 30; this co-solvent may be present in the composition in a organic co-solvent/organic solvent weight/weight (W/W) ratio of between about 1/15 and 1/2. The solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+R'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied can be of the order of about 0.3 to about 1 ml. In one embodiment for the volume, the volume is on the order of about 0.5 ml, for cats and on the order of about 0.3 to about 3 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference), which in one embodiment of the spot-on formulation comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

The liquid carrier vehicle can optionally contain a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent is present in the formulation at a concentration of about 0.05 to 10% weight/volume. In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

Formulations and Administration for Agrochemical Use

The compounds of the formula (I) and (Ia) or their salts can be employed as such or in the form of their preparations (formulations) as combinations with other pesticidally active substances, such as, for example, insecticides, attractants, sterilants, acaricides, nematicides, herbicides, fungicides, and with safeners, fertilizers and/or growth regulators, for example as a premix/readymix.

The insecticides include, for example, phosphoric esters, carbamates, carboxylic esters, chlorinated hydrocarbons, phenylureas, substances prepared by microorganisms.

Examples of insecticides which may optionally be admixed include but are not limited to: phosphoric esters, such as azinphos-ethyl, azinphos-methyl, α-1(4-chlorophenyl)-4-(O-ethyl, S-propyl)phosphoryloxy-pyrazole, chlorpyrifos, coumaphos, demeton, demeton-5-methyl, diazinon, dichlorvos, dimethoate, ethoate, ethoprophos, etrimfos, fenitrothion, fenthion, heptenophas, parathion, parathion-methyl, phosalone, poxim, pirimiphos-ethyl, pirimiphos-methyl, profenofos, prothiofos, sulfprofos, triazophos and trichlorphon;

carbamates, such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds (e.g. dimethyl(phenyl)silyl-methyl 3-phenoxybenzyl ethers, such as dimethyl-(4-ethoxyphenyl)-silylmethyl 3-phenoxybenzyl ether) or (dimethylphenyl)-silyl-methyl 2-phenoxy-6-pyridylmethyl ethers such as, for example, dimethyl-(9-ethoxy-phenyl)-silylmethyl 2-phenoxy-6-pyridylmethyl ether or [(phenyl)-3-(3-phenoxyphenyl)-propyl[(dimethyl)-silanes such as, for example, (4-ethoxyphen-yl)-[3-(4-fluoro-3-phenoxyphenylpropyl]dimethyl-silane, silafluofen;

pyrethroids (which are also useful for their repellent properties, e.g. against mosquitoes), such as allethrin, alphamethrin, bioresmethrin, byfenthrin, cycloprothrin, cyfluthirin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropane-carboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]-4,5-dihydro-N-nitro-1H-imidazole-2-amine (imidacloprid), N-[(6-chloro-3-pyridyl)-methyl]-N$^2$-cyano-N$^1$-methylacetamide (NI-25); abamectin, AC 303, 630 (chlorfenapyr), acephate, acrinathrin, alanycarb, aldoxycarb, aldrin, amitraz, azamethiphos, *Bacillus thuringiensis*, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert-butyl-pyrimidin-5-yl-o-isopropylphosphorothiate, thiocyclam, thiofanox, thiometon, tralomethrin, triflumuron, trimethacarb, vamidothion, *Verticillium Lacanii*, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alphacypermethrin, cyophenothrin, cyromazine, dazomet, DDT, demeton-5-methylsulphone, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous chloride, metam, metarthizium, anisopliae, methacrifos, methamidophos, methidathion, methiocarb, methoprene, methoxychlor, methyl isothiocyanate, metolcarb, mevinphos, monocrotophos, naled, *Neodiprion* sertifer NPV, nicotine, omethoate, oxydemeton-methyl, pentachlorophenol, petroleum oils, phenothrin, phenthoate, phorate.

Other insecticides that may optionally be admixed may also be from the class of the compounds described by U.S. Pat. No. 7,001,903.

Fungicides which may optionally be admixed are include but are not limited to:

(1) Triazoles which include but are not limited to: azaconazole, propiconazole, tebuconazole, cyproconazole, metconazole, amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, paclobutrazol, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

(2) Imidazoles which include but are not limited to: imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

(3) "Methyl (E)-2-phenyl-3-methoxyacrylate" compounds which include but are not limited to:

methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl]-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoxy)pyrrol-1-yl]-3-methoxyacrylate, methyl (E)-2-[2-(3-methoxyphenyl)phenyl]-3-methoxyacrylate, methyl (E)-2-[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxyphenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-[(3-methylpyridin-2-yloxymethyl)phenyl]-3-methoxyacrylate, methyl (E)-2-[2-[6-(2-methylphenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-di-methylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxyacrylate, methyl (E),(E)-2-{2-(3-methoxyphenyl)methyloximinomethyl[-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3- methoxyacrylate, and methyl (E),(E)-2-{2-[(3-nitrophenylmethyloximinomethyl]phenyl}-3-methoxyacrylate;

(4) Succinate Dehydrogenase Inhibitors which include but are not limited to:
  (a) fenfuram, furcarbanil, cyclafluramid, furmecyclox, seedvax, metsulfovax, pyrocarbolid, oxycarboxin, shirlan, mebenil (mepronil), benodanil, flutolanil (Moncut);
  (b) naphthalene derivatives such as terbinafine, naftifine, butenafine, 3-chloro-7-(2-aza-2,7,7-trimethyl-oct-3-en-5-ine);
  (c) sulphenamides such as dichlofluanid, tolylfluanid, folpet, fluorfolpet; captan, captofol;
  (d) benzimidazoles such as carbendazim, benomyl, furathiocarb, fuberidazole, thiophonatmethyl, thiabendazole or their salts;
  (e) morpholine derivatives such as fenpropimorph, falimorph, dimethomorph, dodemorph, aldimorph, fenpropidine and their arylsulphonates, such as, for example, p-toluenesulphonic acid and p-dodecylphenyl-sulphonic acid;
  (f) dithiocarbamates, cufraneb, ferbam, mancopper, mancozeb, maneb, metam, metiram, thiram zeneb, ziram;
  (g) benzothiazoles, such as 2-mercaptobenzothiazole;
  (h) benzamides, such as 2,6-dichloro-N-(4-trifluoromethylbenzyl)-benzamide;
  (i) boron compounds, such as boric acid, boric esters, borax;
  (j) formaldehyde and formaldehyde-releasing compounds, such as benzyl alcohol mono-(poly)-hemiformal, oxazolidine, hexa-hydro-5-triazines, N-methylolchloroacetamide, paraformaldehyde, nitropyrin, oxolinic acid, tecloftalam;
  (k) tris-N-(cyclohexyldiazeniumdioxy)-aluminium, N-(cyclo-hexyldiazeniumdioxy)-tri-butyltin or K salts, bis-N-(cyclohexyldiazeniumdioxy)-copper, N-methylisothiazolin-3-one, 5-chloro-N-methylisothiazolin-3-one, 4,5-dichloro-N-octylisothiazolin-3-one, N-octylisothiazolin-3-one, 4,5-trimethylene-isothiazolinone, 4,5-benzoisothiazolinone, N-methylolchloroacetamide;
  (l) aldehydes, such as cinnamaldehyde, formaldehyde, glutaraldehyde, 6-bromo-cinnamaldehyde;
  (m) thiocyanates, such as thiocyanatomethylthiobenzothiazole, methylenebisthiocyanate, and the like;
  (n) quaternary ammonium compounds, such as benzyldimethyltetradecylammonium chloride, benzyldimethyldodecylanmuonium chloride, didecyldimethylammonium chloride;
  (o) iodine derivatives, such as diiodomethyl p-tolyl sulphone, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;
  (p) phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;
  (q) microbicides having an activated halogen group, such as chloroacetamide, bronopol, bronidox, tectamer, such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;
  (r) pyridines, such as 1-hydroxy-2-pyridinethione (and their Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;
  (s) metal soaps, such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;
  (t) metal salts, such as copper hydroxycarbonate, sodium dichromate, potassium dichromate, potassium chromate, copper sulphate, copper chloride, copper borate, zinc fluorosilicate, copper fluorosilicate, and mixtures with fixatives;
  (u) oxides, such as tributyltin oxide, $Cu_2O$, CuO, ZnO;
  (v) dialkyldithiocarbamates, such as Na and Zn salts of dialkyldithiocarbamates, tetramethylthiuram disulphide, potassium N-methyl-dithiocarbamate;
  (w) nitriles, such as 2,4,5,6-tetrachloroisophthalodinitrile, disodium cyano-dithioimido-carbamate;
  (x) quinolines, such as 8-hydroxyquinoline, and their Cu salts;
  (y) mucochloric acid, 5-hydroxy-2(5H)-furanone;
  (z) 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyl-dithiocarbamate, 2-oxo-2-(4-hydroxy-phenyl)acetohydroximic acid chloride, phenyl-(2-chloro-cyano-vinyl) sulphone, phenyl-(1,2-dichloro-2-cyano-vinyl) sulphone; and
  (aa) Ag-, Zn- or Cu-containing zeolites, alone or enclosed in polymeric active compounds, or
  (bb) mixtures of more than one of the abovementioned fungicides.

Herbicides which are known from the literature and which can be mentioned, which can be combined with the compounds of the formula (I) and (Ia), are, for example, the following active substances (Note: the compounds are either designated by the common name according to the International Organization for Standardization (ISO) or using the chemical name, if appropriate together with a customary code number): acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; amitrol; AMS, i.e. ammonium sulfamate; anilofos; asulam; atrazine; azafenidin; azimsulfuron (DPX-A8947); aziprotryn; barban; BAS 516 H, i.e. 5-fluoro-2-phenyl-4H-3,1-benzoxazin-4-one; beflubutamid; benazolin(-ethyl); benfluralin; benfuresate; bensulfuron(-methyl); bensulide; bentazone(-sodium); benzobicyclone; benzofenap; benzofluor; benzoylprop(-ethyl); benzthiazuron; bialaphos (bilanafos); bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; carfentrazone(-ethyl); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-methyl or -ethyl); cinmethylin; cinosulfuron; clethodim; clefoxydim, clodinafop and its ester derivatives (for example clodinafop-propargyl); clomazone; clomeprop; cloproxydim; clopyralid; clopyrasulfuron(-methyl); cloransulam(-methyl); cumyluron (JC 940); cyanazine; cycloate; cyclosulfamuron (AC 104); cycloxydim; cycluron; cyhalofop and its ester derivatives (for example butyl-ester, DEH-112); cyperquat; cyprazine; cyprazole; daimuron; 2,4-D; 2,4-DB; dalapon; dazomet, desmedipham; desmetryn; di-allate; dicamba; dichlobenil; dichlorprop(-P); diclofop and its esters such as diclofop-methyl; diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethenamid(-P); dimethazone, dimethipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example ethyl ester, HC-252), ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl]ethanesulfonamide; fenoprop; fenoxan, fenoxapropand fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; florasulam; fluazifop and fluazifop-P and their esters, for example fluazifop-butyl and fluazifop-P-butyl; fluazolate, flucarbazone(-sodium); fluchloralin; flufenacet (FOE 5043), flufenpyr, flumetsulam; flumeturon; flumiclorac(-pentyl); flumioxazin (S-482); flumipropyn; fluometuron; fluorochloridone, fluorodifen; fluoroglycofen(-ethyl); flupoxam (KNW-739); flupropacil (UBIC-4243); fluproanate, flupyrsulfuron(-methyl, or -sodium); flurenol(-butyl); fluridone; fluorochloridone; fluoroxypyr(-meptyl); flurprimidol, flurtamone; fluthiacet(-methyl); fluthiamide (also known as flufenacet); fomesafen; foramsulfuron; fosamine; furilazole (MON 13900), furyloxyfen; glufosinate(-ammonium); glyphosate(-isopropylammonium); halosafen; halosulfuron(-methyl) and its esters (for example the methyl ester, NC-319); haloxyfop and its esters; haloxyfop-P (=R-haloxyfop) and its esters; HC-252 (diphenylether), hexazinone; imazamethabenz(-methyl); imazamethapyr; imazamox; imazapic, imazapyr; imazaquin and salts such as the ammonium salts; imazethamethapyr; imazethapyr, imazosulfuron; indanofan; iodosulfuron-(methyl)-(sodium), ioxynil; isocarbamid; isopropalin; isoproturon; isouron; isoxaben; isoxachlortole; isoxaflutole; isoxapyrifop; karbutilate; lactofen; lenacil; linuron; MCPA; MCPB; mecoprop; mefenacet; mefluidid; mesosulfuron(-methyl); mesotrione; metam, metamifop, metamitron; metazachlor; methabenzthiazuron; methazole; methoxyphenone; methyldymron; metobenzuron, metobromuron; (S-)metolachlor; metosulam (XRD 511); metoxuron; metribuzin; metsulfuron-methyl; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazone; oxasulfuron; oxaziclomefone; oxyfluorfen; paraquat; pebulate; pelargonic acid; pendimethalin; penoxulam; pentanochlor, pentoxazone; perfluidone; pethoxamid, phenisopham; phenmedipham; picloram; picolinafen; piperophos; piributicarb; pirifenop-butyl; pretilachlor; primisulfuron(-methyl); procarbazone(-sodium); procyazine; prodiamine; profluazole, profluralin; proglinazine(-ethyl); prometon; prometryn; propachlor; propanil; propaquizafop; propazine; propham; propisochlor; propoxycarbazone(-sodium), propyzamide; prosulfalin; prosulfocarb; prosulfuron (CGA-152005); prynachlor; pyraclonil, pyraflufen(-ethyl); pyrazolinate; pyrazon; pyrazosulfuron(-ethyl); pyrazoxyfen; pyribenzoxim; pyributicarb; pyridafol; pyridate; pyriftalid, pyrimidobac(-methyl); pyrithiobac(-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron(-methyl); sulfosate ($IC_1$-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide; thiazafluoron; thiazopyr (Mon-13200); thidiazimin (SN-24085); thifensulfuron(-methyl); thiobencarb; tiocarbazil; tralkoxydim; tri-allate; triasulfuron; triaziflam; triazofenamide; tribenuron(-methyl); 2,3,6-trichlorobenzoic acid (2,3,6-TBA), triclopyr; tridiphane; trietazine; trifloxysulfuron(-sodium), trifluralin; triflusulfuron and esters (e.g. methyl ester, DPX-66037); trimeturon; tritosulfuron; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127; KIH-2023 and KIH5996.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride and oxabetrinil.

Components which may be employed for the active substances according to the invention in mixed formulations, for example, known active compounds which are based on an inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other compounds which can be employed, whose mechanism of action is to a degree unknown or different, are described, for example, in Weed Research 26, 441-445 (1986), or "The Pesticide Manual", 12th Edition 2000 (hereinbelow also abbreviated to "PM"), The British Crop Protection Council and the Royal Soc. of Chemistry (editors) and literature cited therein.

The compounds of formula (I) and formula (Ia) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Kuchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I) and formula (Ia), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) and (Ia) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) and formula (Ia) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) and formula (Ia) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineers Handbook", 5th Ed., McGraw-Hill, New York 1973, p. 8-57.

In general, the agrochemical preparations comprise a range selected from the group consisting of about 0.1 to about 99% by weight and about 0.1 to about 95% by weight, of compounds of formula (I) and (Ia).

The concentration of compounds of formula (I) and (Ia) in wettable powders is, for example, about 10 to about 90% by weight, the remainder to 100% by weight being composed of customary formulation components. In the case of emulsifiable concentrates, the concentration of compounds of formula (I) and formula (Ia) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and formula (Ia) and about 5% to about 20% by weight of compounds of formula (I). For sprayable solutions comprise a range selected from the group consisting of about 0.05% to about 80% by weight of compounds of formula (I) and formula (Ia) and about 2% to about 50% by weight of compounds of formula (I) and formula (Ia). In the case of water-dispersible granules, the content of compounds of formula (I) and formula (Ia) depends partly on whether the compounds of formula (I) and formula (Ia) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) and formula (Ia) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The mixtures according to the invention can be applied via the soil either pre-emergently or post-emergently. The mixtures according to the invention can also be applied via the leaf. The mixtures according to the invention can be employed for seed dressing. It is also possible to apply the mixtures according to the invention via an irrigation system, for example via the water for irrigation.

Other Active Agents for Pharmaceutical/Veterinary Use

Additional pesticidally or veterinarily active ingredients, which include, but are not limited to, acaricides, anthelmintics, anti-parasitics and insecticides, may also be added to the compositions of the invention in combination with compounds of formula (I) or (Ia). Anti-parasitic agents can include both ectoparasiticisal and endoparasiticidal agents. These agents are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil HCl, allopurinol, alprazolam, altrenogest, amantadine HCl, amikacin sulfate, aminocaproic acid, aminopentamide hydrogen sulfate, aminophylline/theophylline, amiodarone HCl, amitraz, amitriptyline HCl, amlodipine besylate, ammonium chloride, ammonium molybdenate, amoxicillin, amoxicillin, clavulanate potassium, amphotericin B desoxycholate, amphotericin B lipid-based, ampicillin, amprolium HCl, antacids (oral), antivenin, apomorphione HCl, apramycin sulfate, ascorbic acid, asparaginase, aspiring, atenolol, atipamezole HCl, atracurium besylate, atropine sulfate, aurnofin, aurothioglucose, azaperone, azathioprine, azithromycin, baclofen, barbituates, benazepril HCl, betamethasone, bethanechol chloride, bisacodyl, bismuth subsalicylate, bleomycin sulfate, boldenone undecylenate, bromides, bromocriptine mesylate, budenoside, buprenorphine HCl, buspirone HCl, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur HCl, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine HCl, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol HCl, clindamycin, clofazimine, clomipramine HCl, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine HCl, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine HCl, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin HCl, digoxin, dihydrotachysterol (DHT), diltiazem HCl, dimenhydrinate, dimercaprol/BAL, dimethyl sulfoxide, dinoprost tromethamine, diphenylhydramine HCl, disopyramide phosphate, dobutamine HCl, docusate/DSS, dolasetron mesylate, domperidone, dopamine HCl, doramectin, doxapram HCl, doxepin HCl, doxorubicin HCl, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol HCl, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine HCL, gentamicin sulfate, glimepiride, glipizide, glucagon, glucocorticoid agents, glucosamine/chondroitin sulfate, glutamine, glyburide, glycerine (oral), glycopyrrolate, gonadorelin, griseofulvin, guaifenesin, halothane, hemoglobin glutamer-200 (Oxyglobin®), heparin, hetastarch, hyaluronate sodium, hydrazaline HCl, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol HCl, isotretinoin, isoxsuprine HCl, itraconazole, ivermectin, kaolin/pectin, ketamine HCl, ketoconazole, ketoprofen, ketorolac tromethamine, lactulose, leuprolide, levamisole, levetiracetam, levothyroxine sodium, lidocaine HCl, lincomycin HCl, liothyronine sodium, lisinopril, lomustine (CCNU), lufenuron, lysine, magnesium, mannitol, marbofloxacin, mechlorethamine HCl, meclizine HCl, meclofenamic acid, medetomidine HCl, medium chain triglycerides, medroxyprogesterone acetate, megestrol acetate, melarsomine, melatonin, meloxican, melphalan, meperidine HCl, mercaptopurine, meropenem, metformin HCl, methadone HCl, methazolamide, methenamine mandelate/hippurate, methimazole, methionine, methocarbamol, methohexital sodium, methotrexate, methoxyflurane, methylene blue, methylphenidate, methylprednisolone, metoclopramide HCl, metoprolol, metronidaxole, mexiletine HCl, mibolerlone, midazolam HCl milbemycin oxime, mineral oil, minocycline HCl, misoprostol, mitotane, mitoxantrone HCl, morantel tartrate, morphine sulfate, moxidectin, naloxone HCl, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone HCl, oxytretracycline, oxytocin, pamidronate disodium, pancreplipase, pancuronium bromide, paromomycin sulfate, parozetine HCl, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine HCl, pheylbutazone, phenylephrine HCL, phenypropanolamine HCl, phenyloin sodium, pheromones, parenteral phosphate, phytonadione/vitamin K-1, pimobendan, piperazine, pirlimycin HCL, piroxicam, polysulfated glycosaminoglycan, ponazuril, potassium chloride, pralidoxime chloride, praziquantel, prazosin HCl, prednisolone/ prednisone, primidone, procainamide HCl, procarbazine HCl, prochlorperazine, propantheline bromide, *propionibacterium acnes* injection, propofol, propranolol HCl, protamine sulfate, pseudoephedrine HCl, psyllium hydrophilic mucilloid, pyrantel pamoate, pyridostigmine bromide, pyrilamine maleate, pyrimethamine, quinacrine HCl, quinidine, ranitidine HCl, rifampin, s-adenosyl-methionine (SAMe), saline/hyperosmotic laxative, selamectin, selegiline HCL/I-deprenyl, sertraline HCl, sevelamer HCl, sevoflurane, silymarin/milk thistle, sodium bicarbonate, sodium polystyrene sulfonate, sodium stibogluconate, sodium sulfate, sodum thiosulfate, somatotropin, sotalol HCl, spectinomycin HCl, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline HCl, terbutaline sulfate, testosterone, tetracycline HCl, thiabendazole, thiacetarsamide sodium, thiamine HCl, thioguanine, thiopental sodium, thiotepa, thyrotropin, tiamulin, ticarcilin disodium, tiletamine HCl/zolazepam HCl, tilmocsin, tiopronin, tobramycin sulfate, tocamide HCl, tolazoline HCl, telfenamic acid, topiramate, tramadol HCl, trimcinolone acetonide, trientine HCl, trilostane, trimepraxine tartrate w/prednisolone, tripelennamine HCl, tylosin, urdosiol, valproic acid, vanadium, vancomycin HCl, vasopressin, vecuronium bromide, verapamil HCl, vinblastine sulfate, vincristine sulfate, vitamin E/selenium, warfarin sodium, xylazine HCl, yohimbine HCl, zafirlukast, zidovudine (AZT), zinc acetate/zinc sulfate, zonisamide and mixtures thereof.

In one embodiment of the invention, arylpyrazole compounds including phenylpyrazoles such as fipronil and derivatives of fipronil, are known in the art and are suitable for combination with the compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131, which are all incorporated herein by reference in their entirety,—each assigned to Merial, Ltd., Duluth, Ga.).

In another embodiment of the invention, nodulisporic acid and its derivatives (a class of known acaricidal, anthelminitic, anti-parasitic and insecticidal agents) can be added to the compositions of the invention. These compounds are used to treat or prevent infections in humans and animals and are described, for example, in U.S. Pat. Nos. 5,399,582 and 5,962,499. The composition can include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 March 2008, 176-181.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. Nos. 5,703,078 and 5,750,695, all of which are hereby incorported by reference in their entirety.

In another embodiment, the compositions of the invention may be combined with cyclo-depsipeptide anthelmintic compounds including emodepside (see Willson et al., *Parasitology*, January 2003, 126(Pt 1):79-86).

In another embodiment of the invention, one or more macrocyclic lactones, which act as an acaricide, anthelmintic agent and insecticide, can be added to the compositions of the invention. The macrolides are well-known in the art (see e.g. *Macrolides—Chemistry, pharmacology and clinical uses*— edited by Bryskier et al., publ. by Arnette Blackwell, (1993)) and include but are not limited to 12-membered ring macrolides (e.g. methymycin, neomethymycin, YC-17, litorin); 14-membered ring macrolides (e.g. erythromycin A-F, oleandomycin, sporeamicin, roxithromycin, dirithromycin, flurithromycin, clarithromycin, davercin); 15-membered ring macrolides (e.g. azithromycin); 16-membered ring macrolides (e.g. josamycin, kitasamycin, spiramycin, midecamycin, rokitamycin, miokamicin) and 17-membered ring macrolides (e.g. lankadicin).

The macrocyclic lactones also include, but are not limited to, avermectins, such as abamectin, dimadectin, doramectin, emamectin, eprinomectin, ivermectin, latidectin, lepimectin, selamectin and milbemycins, such as milbemectin, milbemycin D, moxidectin and nemadectin. Also included are the 5-oxo and 5-oxime derivatives of said avermectins and milbemycins. Examples of combinations of active pesticides with macrocyclic lactones include but are not limited to those described in U.S. Pat. Nos. 6,426,333; 6,482,425; 6,962,713 and 6,998,131, each of which is incorporated herein by reference—each assigned to Merial, Ltd., Duluth, Ga.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, *Tetrahedron Lett.*, 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring; milbemycins lack the glycosidic moiety of the avermectins. The natural product avermectins are disclosed in U.S. Pat. No. 4,310, 519 to Albers-Schonberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" 12th ed., S. Budavari, Ed., Merck & Co., Inc. Whitehouse Station, New Jersey (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356; 3,818,047; 4,225,598; 4,798,837; 4,751,225, EP 0 179 022 or U.K. 2 140 010 as well as U.S. Pat. Nos. 6,096,329 and 6,685,954 (both assigned to Merial Ltd., Duluth, Ga.), all of which are incorporated herein by reference. Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that can be combined with the compound of the invention to form a composition can be a benzenedisulfonamide compound, which includes but is not limited to clorsulon; or a cestodal agent, which includes but is not limited to praziquantel, pyrantel or morantel.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside.

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060, both which are incorporated herein by reference. It would be well within the skill level of the practitioner to decide which individual compound can be used in the inventive formulation to treat a particular infection of an insect.

Where appropriate the anthelmintic, antiparasitic and insecticidal agent may also be selected from the group of compounds described above as suitable for agrochemical use. In general, the additional pesticidal agent is included in a dose of between about 0.1 μl and about 10 mg. In one embodiment of the invention, the additional pesticidal agent is included in a dose of between about 1 μl and about 10 mg. In another embodiment of the invention, the additional pesticidal agent is included in a dose of about 5 to about 200 μg/kg of weight of animal. In yet another embodiment of the invention, the additional pesticidal agent is included in a dose between about 0.1 to about 10 mg/kg of weight of animal. In still another embodiment of the invention, the additional pesticidal agent is included in a dose between about 0.5 to 50 mg/kg.

The proportions, by weight, of the benzotriazol-2-yl-acetamidonitrile compound and the additional pesticidal agent are for example between about 5/1 and about 10,000/1. However, one of ordinary skill in the art would be able to select the appropriate ratio of benzotriazol-2-yl-acetamidonitrile compound and the additional pesticidal agent for the intended host and use thereof.

Another aspect of the invention is the process of making the arylazol-2-yl-cyanoethylamide compounds of the invention.

Method of Synthesizing the Compounds of the Invention

The compounds of formula (I) and (Ia) may be prepared by the application or adaptation of known methods to form thioamides (i.e. methods heretofore used or described in the chemical literature). A summary of such methods is found on the first page of the publication describing the conversion of nitriles to thioamides with ammonium sulfide in methanol with microwave irradiation "Simple Microwave-Assisted Method for the Synthesis of Primary Thioamides from Nitriles", M. C. Bagley, K. Chapaneri, C. Glover, E. A. Merritt, Synlett, 2004, 14, 2615-2617.

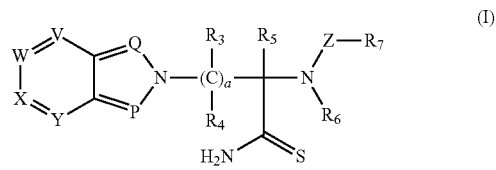

(I)

For example, compounds of formula (I) are obtainable by a process wherein compound of formula (II) is reacted with ammonium sulfide or sodium hydrosulfide wherein $R_3$, $R_4$, $R_5$, $R_6$, $R_7$, P, Q, V, W, X, Y, Z, a, are as defined above for the compounds of formula (I).

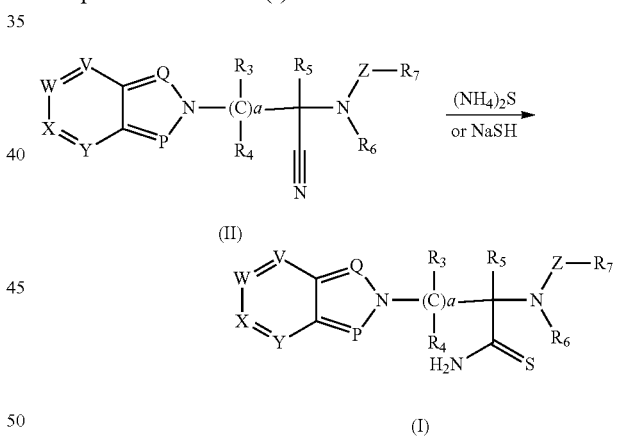

Similarly, compounds of formula (Ia) are obtainable by a process wherein compound of formula (IIa) is reacted with ammonium sulfide wherein $R_3$, $R_4$, $R_5$, $R_6$, $R_7$, P, Q, V, W, X, Y, Z, a, are as defined above for the compounds of formula (Ia)

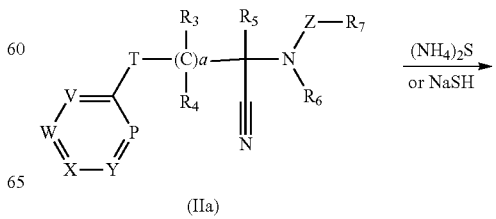

(IIa)

-continued

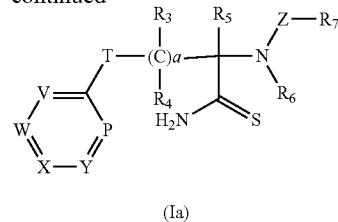

(Ia)

The reaction is generally carried out in a solvent with or without the presence of base.

The solvent to be used in the reaction includes, for example but not limited to, water, alcoholic solvent such as methanol, ethanol and the like, and a combination of water and such alcoholic solvent.

The base that can be used in this reaction includes, for example but not limited to, organic bases such as triethylamine, diisopropylamine, pyridine and the like. The reaction temperature is usually in the range of −50° C. to 200° C., preferably in the range of −20° C. to 130° C. and the reaction time is usually in the range of 0.1 to 72 hours.

The reaction can be carried out under pressure with or without microwave irradiation.

After completion of the reaction, the compounds of formula (I) and (Ia) can be isolated by employing conventional methods such as adding the reaction mixture to water, extracting with an organic solvent, concentrating the extract and the like. The isolated compound of formula (I) and (Ia) can be purified by a technique such as chromatography, recrystallization and the like, if necessary. Compound of formula (II) are described in U.S. Provisional Application SN: 60/930,485 and the compound of formula (IIa) are described in WO 2002/049641, WO 2003/097036, WO 2003/097585, WO 2003/104187, WO 2004/000793, WO 2005/044784, WO 2005/05802, WO 2005/121075 and WO 2006/043654 as well as in EP 953565 (U.S. Pat. No. 6,239,077) and EP 1445251.

Method of Treatment with Compounds of the Invention

Another aspect of the invention is a method for preventing or treating an endoparasitic infestation/infection (e.g. filariae or worms) in an animal (e.g. a mammal or bird), comprising administering an endoparasiticidally effective amount of a compound or a composition of the invention. Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

The endoparasites treated include but are not limited to those helminths selected from the group consisting of *Anaplocepheda, Ancylostoma, Anecator, Ascaris, Caenorhabditis, Capillaria, Cooperia, Dipyllidinum, Dirofilaria, Echinococcus, Enterobius, Fasciola, Haemonchus, Oesophagostumum, Ostertagia, Toxocara, Strongyloides, Toxascaris, Trichinella, Trichuris, Trichostrongylus* and combinations thereof.

In one embodiment of the endoparasites treated the endoparasite is *Haemonchus contortus* (*H. contortus*).

Yet another aspect of the invention is also directed toward a method of treating an animal (e.g. a mammal or bird), against ectoparasitic infection (e.g. insects) by administering an ectoparasiticidally effective amount of the composition of the invention. Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

In another embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (Ctenocephalides fells, *Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like). In yet another embodiment for the treatment against ectoparasites, the ectoparasite is a flea and/or tick. Additional examples of ectoparasites include but are not limited to the tick genus *Boophilus*, especially those of the species microplus (cattle tick), decoloratus and annulatus; myiases such as Dermatobia hominis (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia* irritans (horn fly); lice such as *Linognathus* vitulorum, etc.; and mites such as Sarcoptes scabici and *Psoroptes ovis*. The above list is not exhaustive and other ectoparasites are well known in the art to be harmful to animals and humans. These include, for example migrating dipterous larvae. In another embodiment of the invention, the compounds and compositions of the invention are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:

(1) from the class of Isopoda, for example *Oniscus asellus, Armadillidium vulgare* and *Porcellio scaber;*

(2) from the class of Diplopoda, for example *Blaniulus guttulatus;*

(3) from the class of Chilopoda, for example Geophilus carpophagus and *Scutigera* spp.;

(4) from the class of Symphyla, for example Scutigerella immaculate;

(5) from the class of Thysanura, for example Lepisma saccharina;

(6) from the class of Collembola, for example Onychiurus armatus;

(7) from the class of Blattaria, for example *Blatta orientalis, Periplaneta americana, Leucophaea maderae* and *Blattella germanica;*

(8) from the class of Phthiraptera, for example *Pediculus humanus corporis, Haematopinus* spp., *Linognathus* spp., *Trichodectes* spp. and *Damalinia* spp.;

(9) from the class of Hymenoptera, for example *Diprion* spp., Hop/ocampa spp., *Lasius* spp., *Monomorium pharaonis* and *Vespa* spp.;

(10) from the class of Siphonaptera, for example *Xenopsylla cheopis* and *Ceratophyllus* spp.;

(11) from the class of Anoplura (Phthiraptera), for example, *Damalinia* spp., *Haematopinus* spp., *Linognathus* spp., *Pediculus* spp., *Trichodectes* spp.;

(12) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*;

(13) from the class of Bivalva, for example, *Dreissena* spp.;

(14) from the class of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *C/eonus mendicus, Conoderus* spp., *Cosmopolites* spp., *Costelytra zea*/andica, *Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha , Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(15) from the class of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;

(16) from the class of Gastropoda, for example, *Anion* spp., *Biomphalaria* spp., *Bulinus* spp., *Deroceras* spp., *Galba* spp., *Lymnaea* spp., *Oncomelania* spp., *Succinea* spp.;

(17) from the class of helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*;

(18) from the class of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrats, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(19) from the class of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis* cardui, *Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysfi, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*;

(20) from the class of Isoptera, for example, *Reticulitermes* spp., *Odontotermes* spp.;

(21) from the class of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata,*

Chilo spp., Choristoneura fumiferana, Clysia ambiguella, Cnaphalocerus spp., Earias insulana, Ephestia kuehniella, Euproctis chrysorrhoea, Euxoa spp., Feltia spp., Galleria mellonella, Helicoverpa spp., Heliothis spp., Hofmannophila pseudospretella, Homona magnanima, Hyponomeuta padella, Laphygma spp., Lithocolletis blancardella, Lithophane antennata, Loxagrotis albicosta, Lymantria spp., Malacosoma neustria, Mamestra brassicae, Mocis repanda, Mythimna separata, Oria spp., Oulema oryzae, Panolis flammea, Pectinophora gossypiella, Phyllocnistis citrella, Pieris spp., Plutella xylostella, Prodenia spp., Pseudaletia spp., Pseudoplusia includens, Pyrausta nubilalis, Spodoptera spp., Thermesia gemmatalis, Tinea pellionella, Tineola bisselliella, Tortrix viridana, Trichoplusia spp.;

(22) from the class of Orthoptera, for example, Acheta domesticus, Blatta orientalis, Blattella germanica, Gryllotalpa spp., Leucophaea maderae, Locusta spp., Melanoplus spp., Periplaneta americana, Schistocerca gregaria.;

(23) from the class of Thysanoptera, for example, Baliothrips biformis, Enneothrips flavens, Frankliniella spp., Heliothrips spp., Hercinothrips femoralis, Kakothrips spp., Rhipiphorothrips cruentatus, Scirtothrips spp., Taeniothrips cardamoni, Thrips spp.;

(24) from the class of Protozoa, for example, Eimeria spp.

In each aspect of the invention, the compounds and compositions of the invention can be applied against a single pest or combinations thereof.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development.

The invention is further described by the following non-limiting examples which further illustrate the invention, and are not intended, nor should they be interpreted, to limit the scope of the invention.

EXAMPLES

All temperatures are given in degrees Centigrade; room temperature means 20 to 25° C. Reagents were purchased from commercial sources or prepared following literature procedures. Proton and fluorine magnetic resonance (respectively 1H NMR and 19F NMR) spectra were recorded on a Varian INOVA NMR spectrometer [400 MHz (1H) or 500 MHz (1H) and 377 MHz (19F)]. All spectra were determined in the solvents indicated. Chemical shifts are reported in ppm downfield of tetramethylsilane (TMS), referenced to the residual proton peak of the respective solvent peak for $^1$H NMR. Interproton coupling constants are reported in Hertz (Hz).

LC-MS spectra were either obtained using a Thermofinnigan AQA MS ESI instrument, using a Phenomenex Aqua 5 micron C18 125A 50×4.60 mm column and a linear gradient from 55% methanol: 1% acetonitrile in water to 100% methanol over 3 minutes. 100% methanol was maintained for 2 minutes. Alternatively, LCMS spectra were obtained using an Agilent 1200SL HPLC equipped with a 6130 mass spectrometer operating with electrospray ionization; chromatographic data were obtained using a Shimadzu Shim-pack XR-ODS, 3.0×30 mm, 2.2 micron particle size column and a water: methanol gradient from 15% methanol to 95% methanol in 2.2 minutes under a 1.5 mL/min flow; a hold at 95% methanol was applied at the end of the gradient for 0.8 minutes; and both water and methanol mobile phases contained 0.1% formic acid.

Example 1

N-[1-Methyl-1-thiocarbamoyl-2-(4,5,7-trichloro-2H-benzotriazol-2-yl)-ethyl]-4-trifluoromethoxybenzamide (compound No 1)

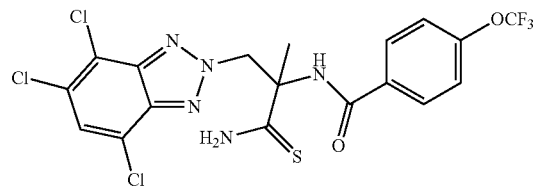

A solution of N-[1-Cyano-1-methyl-2-(4,5,7-trichloro-2H-benzotriazol-2-yl)-ethyl]-4-trifluoromethoxybenzamide (60 mg, 0.12 mmole, described in U.S. Provisional Application SN: 60/930,485 as compound 1.064) and ammonium sulfide (0.04 mL, 40-48 wt. % in water from Sigma-Aldrich) in methanol (4 mL) was irradiated for 20 minute in a self-tunable CEM microwave Discover synthesizer at 80° C. (initial power 100 Watts) and then cooled using a flow of compressed air, evaporated in vacuo and partitioned between ethyl acetate and water. The aqueous layer was further extracted with ethyl acetate. The organic extracts were combined, washed with brine, washed with brine, dried over anhydrous magnesium sulfate, filtered and concentrated under reduced pressure to give a residue that that was purified by chromatography ($SiO_2$, heptane/ethyl acetate) to afford the title compound as a solid (30 mg, 47%) along with recovered starting material (22 mg, 37%). MS (ES): M/Z [M+H] =526 and [M−H]=524. 1H NMR: (400 MHz, DMSO-$d_6$): 1.48 (s, 3H), 5.59 (d, J=13.3 Hz, 1H), 5.70 (, J=13.3 Hz, 1H), 7.44 (d, J=8.0 Hz, 2H), 7.88 (s, 1H), 7.93 (d, J=8.8 Hz, 2H), 8.16 (s, 1H), 9.34 (s, 1H) and 9.83 (s, 1H). 19F NMR (376 MHz, DMSO-d$_6$): −57.2 (s, 3F).

Example 2

N-[1-Methyl-1-thiocarbamoyl-2-(4,5,7-trichloro-2H-benzotriazol-2-yl)-ethyl]-4-trifluoromethylthiobenzamide (compound No 2)

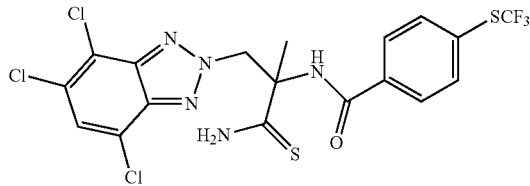

Using a procedure similar to that described in Example 1, except using N-[1-Cyano-1-methyl-2-(4,5,7-trichloro-2H-benzotriazol-2-yl)-ethyl]-4-trifluoromethylthiobenzamide (70 mg, 0.14 mmole, described in U.S. Provisional Application Ser. No. 60/930,485 as compound No 1.065), the title compound was isolated as a solid (37 mg, 49%). MS (ES): M/Z [M+H]=542 and [M−H]=540. 1H NMR: (400 MHz, DMSO-d$_6$): 1.48 (s, 3H), 5.56-5.64 (m, 1H), 5.66-5.76 (m, 1H), 7.80 (d, J=8.3 Hz, 2H), 7.88 (s, 1H), 7.93 (d, J=8.4 Hz, 2H), 8.25 (s, 1H), 9.36 (s, 1H) and 9.84 (s, 1H). 19F NMR (376 MHz, DMSO-d$_6$): −42.2 (s, 3F).

Example 3

N-[2-(4-Cyano-2-trifluoromethylphenoxy)-1-methyl-1-thiocarbamoyl-ethyl]-4-trifluoromethoxybenzamide (compound No 3)

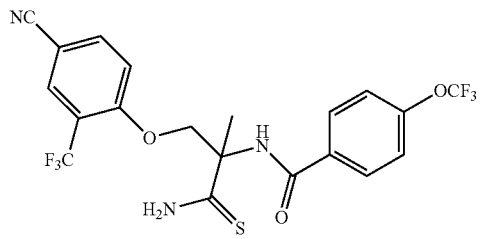

Using a procedure similar to that described in Example 1, except using N-[1-Cyano-2-(4-cyano-2-trifluoromethylphenoxy)-1-methyl-ethyl]-4-trifluoromethoxybenzamide (588 mg, 1.28 mmole, described in WO 2005/044784 as compound 2.6), the title compound was isolated as a solid (180 mg, 28%). MS (ES): M/Z [M+H]=492 and [M−H]=490. 1H NMR: (400 MHz, DMSO-d$_6$): 1.67 (s, 3H), 4.82 (d, J=9.4 Hz, 1H), 4.98 (d, J=9.4 Hz, 1H), 7.38 (d, J=8.5 Hz, 1H), 7.45 (d, J=8.0 Hz, 2H), 7.90-8.01 (m, 2H), 8.07 (d, J=2.1 Hz, 2H), 8.68 (s, 1H), 9.19 (s, 1H) and 9.82 (s, 1H). 19F NMR (376 MHz, DMSO-d$_6$): −61.9 (s, 3F) and −57.1 (s, 3F).

Example 4

N-[1-Methyl-1-thiocarbamoyl-2-(4-thiocarbamoyl-2-trifluoromethylphenoxy)-ethyl]-4-trifluoromethoxybenzamide (compound No 4)

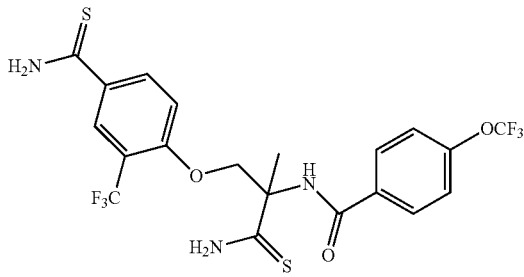

From the same reaction mixture described in Example 3 above was also isolated the corresponding bis-thioamide title compound No 4 (380 mg, 56%). MS (ES): M/Z [M+H]=526 and [M−H]=524. 1H NMR: (400 MHz, DMSO-d$_6$): 1.68 (s, 3H), 4.77 (d, J=9.4 Hz, 1H), 4.94 (d, J=9.4 Hz, 1H), 7.23 (d, J=9.6 Hz, 1H), 7.45 (d, J=8.1 Hz, 2H), 7.91-8.05 (m, 2H), 8.20 (d, J=2.3 Hz, 2H), 8.66 (s, 1H), 9.18 (s, 1H), 9.54 (s, 1H), 9.81 (s, 1H) and 9.85 (br. s., 1H). 19F NMR (376 MHz, DMSO-d$_6$): −61.4 (s, 3F) and −57.1 (s, 3F).

Example 5

N-[2-(5-Cyano-2-trifluoromethylphenoxy)-1-methyl-1-thiocarbamoyl-ethyl]-4-trifluoromethylthiobenzamide (compound No 5)

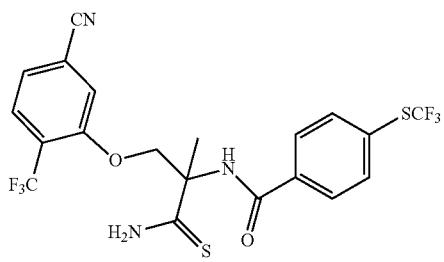

Using a procedure similar to that described in Example 1, except using N-[1-Cyano-2-(5-cyano-2-trifluoromethylphenoxy)-1-methyl-ethyl]-4-trifluoromethylthiobenzamide (672 mg, 1.42 mmole, described in WO 2005/044784 as compound 3.16), the title compound was isolated as a solid (124 mg, 17%). MS (ES): M/Z [M+H]=508 and [M−H]=506. 1H NMR: (400 MHz, DMSO-d$_6$): 1.68 (s, 3H), 4.78 (d, J=9.5 Hz, 1H), 4.93 (d, J=9.4 Hz, 1H), 7.55 (d, J=8.0 Hz, 1H), 7.74 (s, 1H), 7.77 (d, J=8.1 Hz, 1H), 7.80 (d, J=8.2 Hz, 2H), 7.95

(d, J=8.4 Hz, 2H), 8.75 (s, 1H), 9.17 (s, 1H) and 9.83 (s, 1H). 19F NMR (376 MHz, DMSO-d$_6$): −62.1 (s, 3F) and −42.1 (s, 3F).

Example 6

4-Hydroxy-N-[1-methyl-2-(2-methyl-5-thiocarbamoyl-phenoxy)-1-thiocarbamoyl-ethyl]-4-trifluoromethylthiobenzamide (compound No 6)

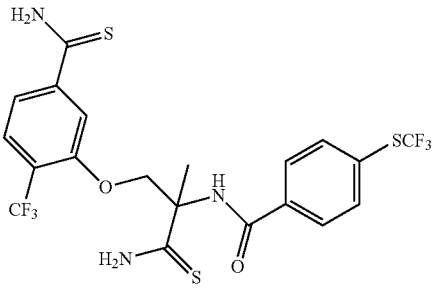

From the same reaction mixture described in Example 5 above was also isolated the corresponding bis-thioamide title compound No 6 (152 mg, 20%). MS (ES): M/Z [M+H]=542 and [M−H]=540. 1H NMR: (400 MHz, DMSO-d$_6$): 1.69 (s, 3H), 4.75 (d, J=9.2 Hz, 1H), 4.93 (d, J=9.1 Hz, 1H), 7.50 (d, J=8.1 Hz, 1H), 7.56 (s, 1H), 7.61 (d, J=8.2 Hz, 1H), 7.80 (d, J=8.1 Hz, 2H), 7.97 (d, J=8.2 Hz, 2H), 8.73 (s, 1H), 9.20 (br. s., 1H), 9.76 (br. s., 1H), 9.82 (br. s., 1H) and 10.11 (br. s., 1H). 19F NMR (376 MHz, DMSO-d$_6$): −61.4 (s, 3F) and −42.1 (s, 3F).

Example 7

N-[2-(5-Cyano-2-trifluoromethylphenoxy)-1-methyl-1-thiocarbamoyl-ethyl]-4-trifluoromethoxybenzamide (compound No 7)

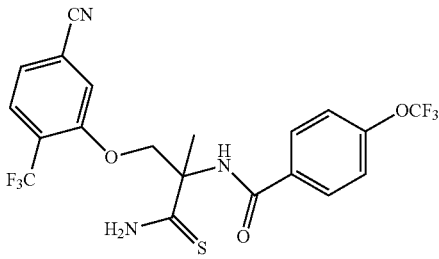

Using a procedure similar to that described in Example 1, except using N-[1-Cyano-2-(5-cyano-2-trifluoromethylphenoxy)-1-methyl-ethyl]-4-trifluoromethoxybenzamide (230 mg, 0.5 mmole, described in WO 2005/044784 as compound 2.6), the title compound was isolated as a solid (39 mg, 16%). MS (ES): M/Z [M+H]=492 and [M−H]=490. 1H NMR: (400 MHz, DMSO-d$_6$): 1.68 (s, 3H), 4.79 (d, J=9.5 Hz, 1H), 4.92 (d, J=9.5 Hz, 1H), 7.45 (d, J=8.0 Hz, 1H), 7.55 (d, J=8.2 Hz, 1H), 7.77 (d, J=8.1 Hz, 2H), 7.88-8.08 (m, 2H), 8.67 (s, 1H), 9.15 (s, 1H) and 9.83 (s, 1H). 19F NMR (376 MHz, DMSO-d$_6$): −62.1 (s, 3F) and −57.1 (s, 3F).

Example 8

4-Hydroxy-N-[1-methyl-2-(2-methyl-5-thiocarbamoyl-phenoxy)-1-thiocarbamoyl-ethyl]-4-trifluoromethoxybenzamide (compound No 8)

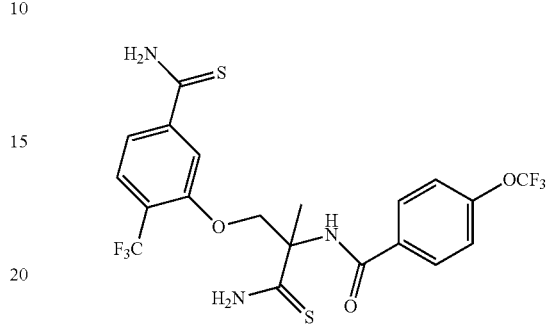

From the same reaction mixture described in Example 7 above was also isolated the corresponding bis-thioamide title compound No 8 (21 mg, 8%). MS (ES): M/Z [M+H]=526 and [M−H]=524. 1H NMR: (400 MHz, DMSO-d$_6$): 1.68 (s, 3H), 4.75 (d, J=9.3 Hz, 1H), 4.92 (d, J=9.2 Hz, 1H), 7.45 (d, J=8.0 Hz, 2H), 7.51 (s, 1H), 7.56 (s, 1H), 7.61 (d, J=8.2 Hz, 1H), 7.94-8.05 (m, 2H), 8.66 (s, 1H), 9.18 (s, 1H), 9.76 (br. s., 1H), 9.81 (s, 1 H) and 10.11 (br. s., 1H). 19F NMR (376 MHz, DMSO-d$_6$): −61.4 (s, 3F) and −57.1 (s, 3F).

Method of Use Examples

Method A: Screening Method to Test Activity of Compounds Against *Haemonchus contortus*.

Twenty L1 *Haemonchus contortus* larvae were added to wells of a microtitre plate containing a nutrient medium and the test compound in DMSO. The microtitre plate was then held at 27° C. where the L1 larvae were allowed to develop. An analysis was conducted at 4 days to determine successful development to the L3 stage. Larvae exposed to DMSO and no test compound served as controls. Compounds numbers 3, 4, 6 and 8 gave at least 90% motility inhibition at a test concentration of 0.15 ppm at the 4 days assessment. Compounds numbers 1, 2, 5 and 7 gave at least 90% motility inhibition at a test concentration of 0.01 ppm at the 4 days assessment.

Method B: Screening Method to Test Activity of Compounds Against *Haemonchus contortus* In Vivo on Mongolian Jirds (*Meriones unguiculatus*).

Mongolian jirds, at least five weeks old, were immunosuppressed and artificially infected with ca. 1000 ensheathed *Haemonchus contortus* third instar larvae. Six days after infection, the jirds were treated by oral gavage with the test compounds, dissolved in a mixture of 2 parts DMSO and 1 part polyethylene glycol (PEG400), at doses of 100 mg/kg and 10 mg/kg. Jirds treated only with the placebo (2 parts DMSO and 1 part PEG400) served as controls. On day 9 (3 days after treatment) the jirds were euthanized and necropsied for recovery of parasites from the stomach. Efficacy was calculated as the average % reduction in the number of worms in each test group compared with the average number of worms from the control group. In this screen, a vast reduction in nematode infestation was achieved with compounds of formula (I) and (Ia). Compound number 1, provided at least 95% reduction in nematode infestation at a dose as low as 1 or 10 mg/kg.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:
1. A thioamide compound of formula (Ia):

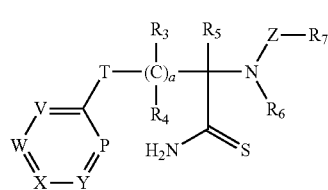

(Ia)

wherein
$R_1$, $R_8$, $R_9$, $R_{10}$ and $R_{11}$, independently of one another, are hydrogen, cyano, nitro, halogen, $C_1$-$C_6$-alkyl, $C_3$-$C_7$-cycloalkyl, halo-$C_1$-$C_6$-alkyl, $C_1$-$C_6$-alkylthio, halo $C_1$-$C_6$-alkylthio, $C_1$-$C_6$-alkylsulfinyl, halo $C_1$-$C_6$-alkylsulfinyl, $C_1$-$C_6$-alkylsulfonyl, halo $C_1$-$C_6$-alkylsulfonyl, $SF_5$, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, unsubstituted or substituted aryl, or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, and methylthioamino;
$R_3$, $R_4$ and $R_5$, independently of one another, are hydrogen, halogen, $C_1$-$C_6$-alkyl, halo-$C_1$-$C_6$-alkyl; $C_3$-$C_7$-cycloalkyl that is either unsubstituted or substituted, whereby the substituents may each be independent of one another and are selected from the group consisting of halogen and $C_1$-$C_6$-alkyl; and phenyl that is either unsubstituted or substituted, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, $C_1$-$C_6$-alkylamino, and di($C_1$-$C_6$-alkyl)amino;
or $R_4$ and $R_5$ together signify $C_2$-$C_6$-alkylene;
$R_6$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or benzyl that is either unsubstituted or substituted, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, $C_1$-$C_6$-alkylamino, and di($C_1$-$C_6$-alkyl)amino;
$R_7$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl, phenyl that is either unsubstituted or substituted, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino; heteroaryl that is either unsubstituted or substituted, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $SF_5$, $C_1$-$C_6$-alkylamino, and di($C_1$-$C_6$-alkyl)amino; or naphthyl or quinolyl that is either unsubstituted or substituted, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, and di($C_1$-$C_6$-alkyl)amino;
P is C—$R_1$ or N;
V is C—$R_8$ or N;
W is C—$R_9$ or N;
X is C—$R_{10}$ or N;
Y is C—$R_{11}$ or N;
Z is a direct bond, C(O), C(S) or S(O)$_p$;
T is independently O, S or NH;
a is 1, 2 or 3; and
p is 1 or 2.
2. The compound of claim 1, wherein:
$R_1$, $R_8$, $R_9$, $R_{10}$ and $R_{11}$, independently of one another, is hydrogen, cyano, chloro or trifluoromethyl;
$R_3$, $R_4$ and $R_6$ is H;
$R_5$ is hydrogen, $C_1$-$C_6$alkyl or halo-$C_1$-$C_6$-alkyl;
P is N or C—$R_1$;
V is C—$R_8$;
W is C—$R_9$;
X is C—$R_{10}$;
Y is C—$R_{11}$;
Z is C(O);
T is O;
$R_7$ is phenyl that is unsubstituted or substituted, wherein the substituents may each be independent of one another and are selected from the group consisting of halogen, $C_1$-$C_6$-alkylthio, halo-$C_1$-$C_6$-alkylthio, $C_1$-$C_6$-alkoxy, and halo-$C_1$-$C_6$-alkoxy, and
a is 1.
3. The compound of claim 1, wherein:
$R_1$, $R_8$, $R_9$, $R_{10}$ and $R_{11}$, independently of one another, is hydrogen, cyano, chloro or trifluoromethyl;
$R_3$, $R_4$ and $R_6$ is H;
$R_5$ is methyl;
P is C—$R_1$;
V is C—$R_8$;
W is C—$R_9$;
X is C—$R_{10}$;

Y is C—$R_{11}$;

Z is C(O);

T is O;

$R_7$ is phenyl that is unsubstituted or substituted, wherein the substituents may each be independent of one another and are selected from the group consisting of halo-$C_1$-$C_6$-alkylthio and halo-$C_1$-$C_6$-alkoxy, and a is 1.

4. The compound of claim 1, wherein $R_5$ is $C_1$-$C_6$-alkyl or halo-$C_1$-$C_6$-alkyl.

5. The compound of claim 1, wherein $R_3$ and $R_4$ are each independently hydrogen.

6. The compound of claim 4, wherein $R_5$ is methyl.

7. The compound of claim 5, wherein $R_5$ is methyl.

8. The compound of claim 1, wherein T is O.

9. The compound of claim 1, wherein:

T is O;

Z is C(O);

$R_3$ and $R_4$ are each hydrogen; and $R_5$ is methyl.

10. The compound of claim 3 wherein:

T is O;

Z is C(O);

$R_3$, $R_4$ and $R_6$ are each hydrogen;

$R_5$ is methyl; and $R_7$ is unsubstituted phenyl or phenyl substituted with —$OCF_3$ or —$SCF_3$.

11. A pesticidal composition comprising an effective amount of a compound of claim 1 and a pesticidally or veterinarily acceptable carrier.

12. The composition of claim 11 which further comprises a pesticidal compound.

13. The composition of claim 12, wherein the pesticidal compound is an arylpyrazole, a nodulisporic acid, an amino acetonitrile compound, a macrocyclic lactone, an insect growth regulator, or a paraherquamide compound.

14. The composition of claim 13 wherein the arylpyrazole is fipronil; or the macrocyclic lactone is abamectin, dimadectin, doramectin, emamectin, eprinomectin, ivermectin, latidectin, lepimectin, selamectin, milbemectin, milbemycin D, milbemycin oxime, moxidectin, nemadectin, or combinations thereof.

15. A method of producing the compounds of claim 1, wherein the compounds of formula (Ia) are produced by a process which comprises (i) reacting a compound of formula (IIa)

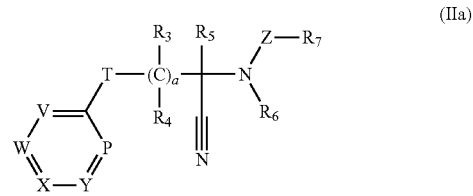

with ammonium sulfide wherein $R_3$, $R_4$, $R_5$, $R_6$, $R_7$, P, Q, V, W, X, Y, Z, a, are as defined above for the compounds of formula (Ia) in a solvent with or without the presence of base.

16. A method of treating an animal against endoparasitic infection by administering an endoparasiticidally effective amount of the compound of claim 1 to an animal in need thereof.

17. The method of claim 16, wherein the endoparasitic infection is a helminth selected from *Anaplocepheda, Ancylostoma, Anecator, Ascaris, Caenorhabditis, Capillaria, Cooperia, Dipyllidinum, Dirofilaria, Echinococcus, Enterobius, Fasciola, Haemonchus, Oesophagostumum, Ostertagia, Toxocara, Strongyloides, Toxascaris, Trichinella, Trichuris, Trichostrongylus* and combinations thereof.

18. The method of claim 17 wherein the helminth is *Haemonchus contortus*.

19. A method of treating an animal against ectoparasitic infection by administering an ectoparasiticidally effective amount of the compound of claim 1 to an animal in need thereof.

20. The method of claim 19 wherein the ectoparasites are selected from fleas, ticks, mites, mosquitoes, flies, lice, blowfly and combinations thereof.

21. The method of claim 19 wherein the ectoparasites are selected from *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes, Felicola*, and combinations thereof.

22. The method of claim 16 or 19 further comprising administering to an animal in need thereof at least one veterinarily active ingredient in addition to the compound of claim 1.

23. The method of claim 22 wherein the at least one veterinarily active ingredient is an arylpyrazole, a nodulisporic acid, an amino acetonitrile compound, a macrocyclic lactone, an insect growth regulator, an or a paraherquamide compound.

24. The method of claim 23 wherein the arylpyrazole is fipronil; or the macrocyclic lactone is abamectin, dimadectin, doramectin, emamectin, eprinomectin, ivermectin, latidectin, lepimectin, selamectin, milbemectin, milbemycin D, milbemycin oxime, moxidectin, nemadectin, or combinations thereof.

* * * * *